United States Patent
Partanen et al.

(10) Patent No.: US 10,694,974 B2
(45) Date of Patent: Jun. 30, 2020

(54) METHOD AND SYSTEM FOR MRI-BASED TARGETING, MONITORING, AND QUANTIFICATION OF THERMAL AND MECHANICAL BIOEFFECTS IN TISSUE INDUCED BY HIGH INTENSITY FOCUSED ULTRASOUND

(71) Applicants: UNIVERSITY OF WASHINGTON, Seattle, WA (US); KONINKLIJKE PHILIPS N.V., Eindhoven (NL)

(72) Inventors: Ari Partanen, Andover, MA (US); Vera Khokhlova, Seattle, WA (US); Navid Farr, Seattle, WA (US); Donghoon Lee, Seattle, WA (US); Wayne Kreider, Seattle, WA (US); Tatiana Khokhlova, Seattle, WA (US); Adam Maxwell, Seattle, WA (US); Yak-Nam Wang, Seattle, WA (US); George Schade, Seattle, WA (US); Michael Bailey, Seattle, WA (US)

(73) Assignees: UNIVERSITY OF WASHINGTON, Seattle, WA (US); KONINKLIJKE PHILIPS N.V., Eindhoven (NL)

( * ) Notice: Subject to any disclaimer, the term of this patent is extended or adjusted under 35 U.S.C. 154(b) by 646 days.

(21) Appl. No.: 15/120,812

(22) PCT Filed: Mar. 27, 2015

(86) PCT No.: PCT/US2015/023021
§ 371 (c)(1),
(2) Date: Aug. 23, 2016

(87) PCT Pub. No.: WO2015/148938
PCT Pub. Date: Oct. 1, 2015

(65) Prior Publication Data
US 2017/0000376 A1 Jan. 5, 2017

Related U.S. Application Data

(60) Provisional application No. 61/971,432, filed on Mar. 27, 2014.

(51) Int. Cl.
A61B 5/055 (2006.01)
A61N 7/02 (2006.01)
(Continued)

(52) U.S. Cl.
CPC ............ *A61B 5/055* (2013.01); *A61B 5/0042* (2013.01); *A61B 5/015* (2013.01); *A61B 5/4836* (2013.01);
(Continued)

(58) Field of Classification Search
CPC ....... A61B 5/055; A61B 5/4836; A61B 5/015; A61B 2090/374; G01R 33/4814; G01R 33/4804; A61N 7/02
See application file for complete search history.

(56) References Cited

U.S. PATENT DOCUMENTS 6,501,978 B2  12/2002  Wagshul et al.
6,516,211 B1  2/2003  Acker et al.
(Continued)

FOREIGN PATENT DOCUMENTS

WO   2013153506 A1   10/2013

OTHER PUBLICATIONS

Canney, et al., "Shock-induced heating and millisecond boiling in gels and tissue due to high intensity focused ultrasound," Ultrasound Med. Biol., vol. 36, No. 2, pp. 250-267, 2010.
(Continued)

*Primary Examiner* — Bill Thomson
*Assistant Examiner* — Aminah Asghar
(74) *Attorney, Agent, or Firm* — McDonnell Boehnen Hulbert & Berghoff LLP

(57) ABSTRACT

Example embodiments of system and method for magnetic resonance imaging (MRI) techniques for planning, real-time monitoring, control, and post-treatment assessment of high intensity focused ultrasound (HIFU) mechanical fraction-
(Continued)

ation of biological material are disclosed. An adapted form of HIFU, referred to as "boiling histotripsy" (BH), can be used to cause mechanical fractionation of biological material. In contrast to conventional HIFU, which cause pure thermal ablation, BH can generate therapeutic destruction of biological tissue with a degree of control and precision that allows the process to be accurately measured and monitored in real-time as well as the outcome of the treatment can be evaluated using a variety of MRI techniques. Real-time monitoring also allow for real-time control of BH.

23 Claims, 21 Drawing Sheets

(51) Int. Cl.
*A61B 5/01* (2006.01)
*A61B 5/00* (2006.01)
*G01R 33/28* (2006.01)
*G01R 33/48* (2006.01)
*A61B 90/00* (2016.01)
*G01R 33/50* (2006.01)
*G01R 33/563* (2006.01)
*G01R 33/56* (2006.01)

(52) U.S. Cl.
CPC ............. *A61N 7/02* (2013.01); *G01R 33/288* (2013.01); *G01R 33/4804* (2013.01); *G01R 33/4814* (2013.01); *A61B 2090/374* (2016.02); *A61B 2576/026* (2013.01); *G01R 33/50* (2013.01); *G01R 33/5602* (2013.01); *G01R 33/56341* (2013.01)

(56) References Cited

U.S. PATENT DOCUMENTS

| | | | | |
|---|---|---|---|---|
| 2008/0146912 | A1* | 6/2008 | Richard | A61B 5/015 600/411 |
| 2010/0125192 | A1* | 5/2010 | Chopra | A61N 7/02 600/411 |
| 2011/0257523 | A1* | 10/2011 | Hastings | A61B 8/0891 600/439 |
| 2012/0259250 | A1* | 10/2012 | Sapozhnikov | A61N 7/02 601/2 |
| 2013/0041249 | A1* | 2/2013 | Salomir | A61N 7/02 600/411 |
| 2013/0217950 | A1* | 8/2013 | Partanen | G01R 33/4814 600/1 |
| 2017/0348040 | A1* | 12/2017 | Govari | A61B 18/20 |

OTHER PUBLICATIONS

Damianou, et al., "MRI monitoring of lesions created at temperature below the boiling point and of lesions created above the boiling point using high intensity focused ultrasound," Journal of Biomedical Science and Engineering, pp. 764-765, 767, 2010.

Khokhlova, et al., "Controlled tissue emulsification produced by high intensity focused ultrasound shock waves and millisecond boiling," J. Acoust. Soc. Am., 2011, v.130(5), pp. 3498-3510, 2011.

Kim, et al., Volumetric MRI-HIFU ablation of uterine fibroids: role of treatment cell size in the improvement of energy efficiency, Eur J Radiol, vol. Nov 81, No. 11, pp. 3652-3659, 2012.

Kohler, et al., "HIFU ablation under 3D guidance of rapid MRI thermometry," Med Phys., vol. 2009, vol. 36, No. 8, pp. 3521-3535, 2009.

Kreider, et al., "Characterization of a multi-element clinical HIFU system using acoustic holography and nonlinear modeling," IEEE Trans. Ultrason., Ferroelect., Freq. Contr., vol. 60, No. 8, pp. 1683-1698, 2013.

PCT/US15/23021 International Search Report and Written Opinion of the International Searching Authority, 30 pages, dated Sep. 29, 2015.

Maxwell, et al., "Disintegration of tissue using high intensity focused ultrasound: Two approaches that utilize shock waves," Acoustics Today, vol. 8, No. 4, pp. 24-36, 2012.

Simon, et al. "Ultrasonic atomization of tissue and its role in tissue fractionation by high intensity focused ultrasound." Physics in medicine and biology, vol. 57, No. 23, 8061-8078, 2012.

Wang, et al., "Histological and biochemical analysis of mechanical and thermal bioeffects in boiling histotripsy lesions induced by high intensity focused ultrasound." Ultrasound in medicine & biology, vol. 39, No. 3, pp. 424-438, 2013.

* cited by examiner

Lesions with content

Flushed lesions

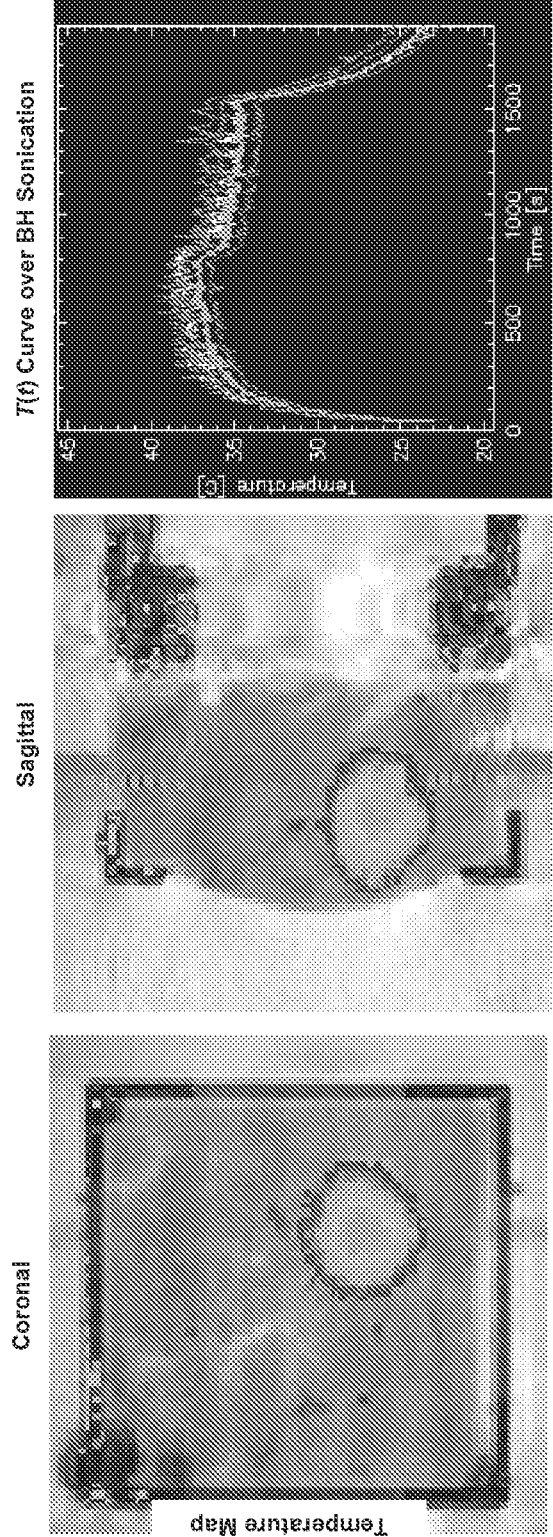
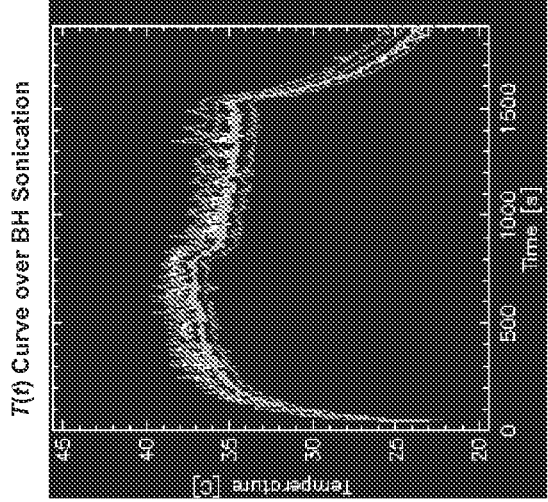
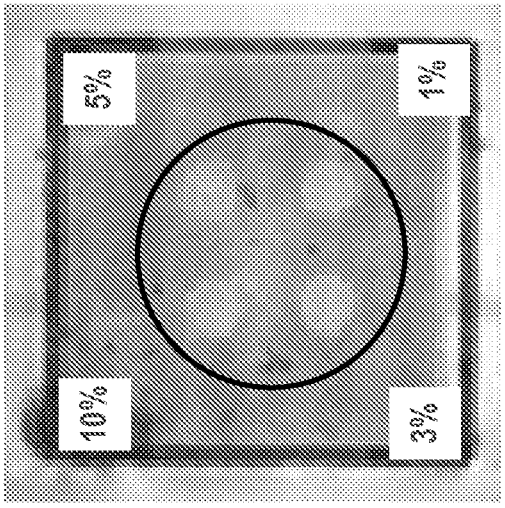
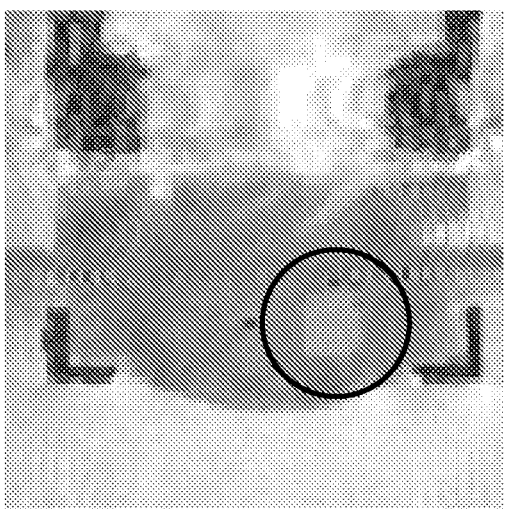
FIG. 12A  FIG. 12B  FIG. 12C  FIG. 12D  FIG. 12E  FIG. 12F

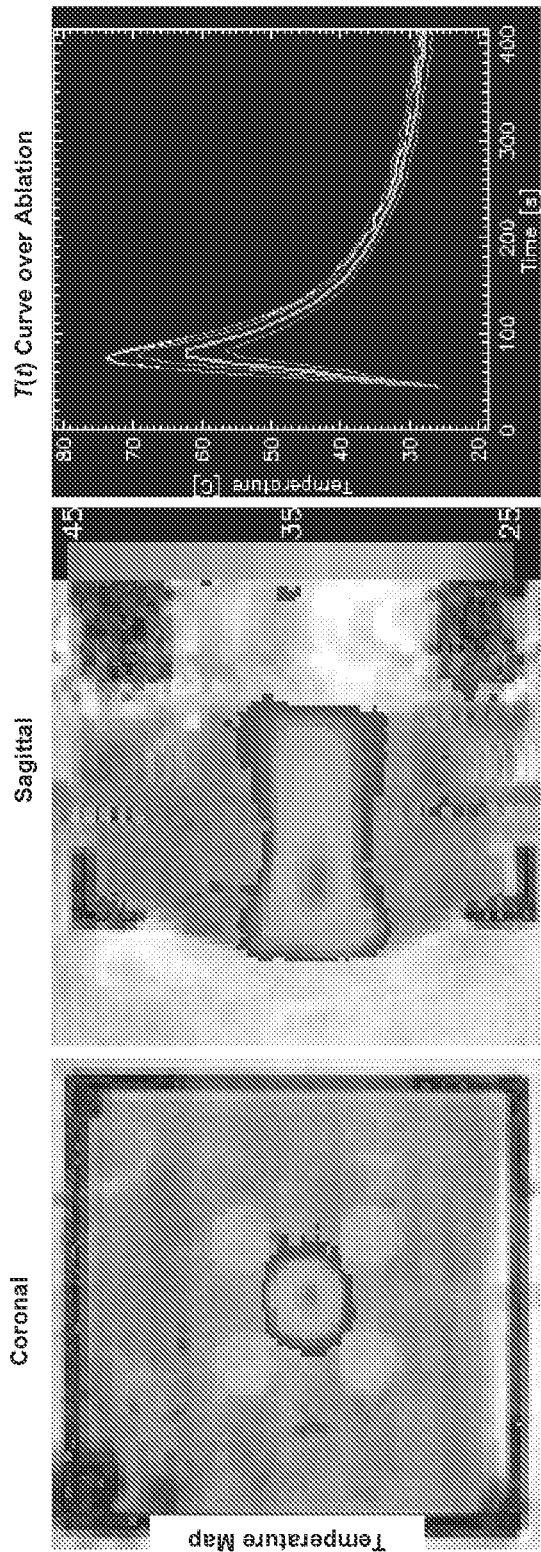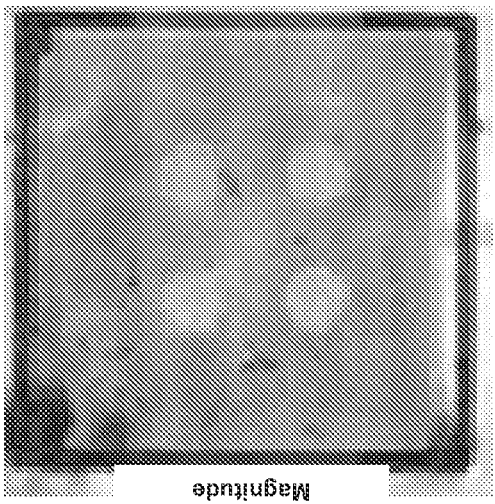
FIG. 13A  FIG. 13B  FIG. 13C  FIG. 13D

FIG. 14B T1-Weighted

FIG. 14A T2-Weighted

METHOD AND SYSTEM FOR MRI-BASED TARGETING, MONITORING, AND QUANTIFICATION OF THERMAL AND MECHANICAL BIOEFFECTS IN TISSUE INDUCED BY HIGH INTENSITY FOCUSED ULTRASOUND

CROSS-REFERENCE TO RELATED APPLICATIONS

This application is a U.S. national phase of International Application No. PCT/US2015/023021, filed on Mar. 27, 2015, which claims priority to U.S. Provisional Application No. 61/971,432, filed Mar. 27, 2014, both of which are incorporated by reference herein in their entirety.

FEDERAL FUNDING STATEMENT

This invention was made with government support under grant nos. 1 K01 EB 015745-01 and 2R01EB007643-05 and T32 DK007779-11A1, awarded by the National Institutes of Health; and grant no. SMST03402, awarded by the National Space Biomedical Research Institute. The government has certain rights in the invention.

BACKGROUND

High intensity focused ultrasound (HIFU) is a medical technology capable of transcutaneous localized ablation of target sites without damaging intervening tissues. In most high intensity focused ultrasound applications, tissue is thermally ablated due to heating caused by ultrasound energy absorption. Various techniques exist for HIFU waves to ablate, damage, or disintegrate an object such as a diseased biological tissue or a foreign body within a patient. More specifically, energy carried by HIFU waves may be absorbed by a given portion of the object, so that the temperature of the given portion is increased, causing thermal ablation of the given portion. HIFU waves can also be sequentially focused (e.g., deflected or scanned) upon different portions of the object so that a larger macroscopic region of the object is thermally ablated. Conventional HIFU processes that primarily cause thermal ablation generally involve the use of HIFU waves with power densities of less than 1 kW/cm$^2$.

An important aspect of HIFU therapy is imaging the treatment site for targeting the HIFU beam (treatment planning), monitoring the treatment in real time (treatment monitoring), controlling the location of targeted region as well as delivered dose to this region (treatment control), and evaluating the final therapeutic effect (post-treatment assessment). In particular, various forms of magnetic resonance imaging (MRI) and related MR diagnostic techniques can be used for this purpose.

BRIEF SUMMARY

In one aspect, the invention provides a method comprising: applying high-intensity focused ultrasound (HIFU) histotripsy to a mass of biological material in order to mechanically fractionate a target volume of the biological material within the mass; concurrently with applying the HIFU histotripsy to the mass of biological material, acquiring magnetic resonance imaging (MRI) data of the mass of biological material in a region including the target volume; identifying in the acquired MRI data features corresponding to HIFU-histotripsy-induced mechanical fractionation of the biological material within the mass; and based on the identified features in the acquired MRI data, monitoring spatial and temporal progress of HIFU-histotripsy-induced mechanical fractionation of the biological material within the target volume.

In another aspect, the invention provides a method comprising: applying high-intensity focused ultrasound (HIFU) histotripsy to a mass of biological material in order to mechanically fractionate a target volume of biological material within the mass; concurrently with applying the HIFU histotripsy to the mass of biological material, acquiring one or more magnetic resonance (MR) mechanical-metric renderings of the mass of biological material in a region including the target volume; identifying in at least one of the one or more acquired MR mechanical-metric renderings features corresponding to HIFU-histotripsy-induced displacement of the biological material within the mass; and based on the identified features in the at least one of the one or more acquired MR mechanical-metric renderings, monitoring a spatial location within the mass of biological material of a focal point of the HIFU histotripsy.

In a still further aspect, the invention provides a method comprising: applying high-intensity focused ultrasound (HIFU) histotripsy to a mass of biological material in order to mechanically fractionate a target volume of the biological material within the mass; subsequent to applying the HIFU histotripsy to the mass of biological material, acquiring magnetic resonance (MRI) data of the mass of biological material in a region including the target volume; identifying in the acquired MRI data features corresponding to HIFU-histotripsy-induced mechanical fractionation of the biological material within the mass; and based on the identified features in the acquired MRI data, determining a location and a spatial extent of HIFU-histotripsy-induced mechanical fractionation of the biological material within the target volume.

In yet another respect, the invention provides an apparatus comprising: a high-intensity focused ultrasound (HIFU) histotripsy subsystem; a magnetic resonance imaging (MRI) subsystem; one or more processors; memory accessible to the one or more processors, and storing machine language instructions that, upon execution by the one or more processors, cause the apparatus to carry out operations including: applying HIFU histotripsy to a mass of biological material in order to mechanically fractionate a target volume of the biological material within the mass, concurrently with applying the HIFU histotripsy to the mass of biological material, acquiring MRI data of the mass of biological material in a region including the target volume, identifying in the acquired MRI data features corresponding to HIFU-histotripsy-induced mechanical fractionation of the biological material within the mass, and based on the identified features in the acquired MRI data, monitoring spatial and temporal progress of HIFU-histotripsy-induced mechanical fractionation of the biological material within the target volume.

In still another respect, the invention provides an apparatus comprising: a high-intensity focused ultrasound (HIFU) histotripsy subsystem; a magnetic resonance imaging (MRI) subsystem; one or more processors; memory accessible to the one or more processors, and storing machine language instructions that, upon execution by the one or more processors, cause the apparatus to carry out operations including: applying HIFU histotripsy to a mass of biological material in order to mechanically fractionate a target volume of biological material within the mass, concurrently with applying the HIFU histotripsy to the mass of biological material, acquiring with the MRI subsystem one or more magnetic resonance (MR) mechanical-metric renderings of the mass of biological material in a region including the target volume, identifying in at least one of the one or more acquired MR mechanical-metric renderings corresponding to HIFU-histotripsy-induced displacement of the biological material within the mass, and based on the identified features in the at least one of the one or more acquired MR mechanical-metric renderings, monitoring a spatial location within the mass of biological material of a focal point of the HIFU histotripsy.

In yet a further respect, the invention provides an apparatus comprising: a high-intensity focused ultrasound (HIFU) histotripsy subsystem; a magnetic resonance imaging (MRI) subsystem; one or more processors; memory accessible to the one or more processors, and storing machine language instructions that, upon execution by the one or more processors, cause the apparatus to carry out operations including: applying HIFU histotripsy to a mass of biological material in order to mechanically fractionate a target volume of the biological material within the mass, subsequent to applying the HIFU histotripsy to the mass of biological material, acquiring MRI data of the mass of biological material in a region including the target volume, identifying in the acquired MRI data features corresponding to HIFU-histotripsy-induced mechanical fractionation of the biological material within the mass, and based on the identified features in the acquired MRI data, determining a location and a spatial extent of HIFU-histotripsy-induced mechanical fractionation of the biological material within the target volume.

In one more respect, the invention provides a non-transitory computer readable medium having stored thereon instructions that, upon execution by one or more processors of an apparatus, cause the apparatus to carry out operations, wherein the apparatus comprises a high-intensity focused ultrasound (HIFU) histotripsy subsystem and a magnetic resonance imaging (MRI) subsystem, and wherein the operations include: applying HIFU histotripsy to a mass of biological material in order to mechanically fractionate a target volume of the biological material within the mass; concurrently with applying the HIFU histotripsy to the mass of biological material, acquiring MRI data of the mass of biological material in a region including the target volume; identifying in the acquired MRI data features corresponding to HIFU-histotripsy-induced mechanical fractionation of the biological material within the mass; and based on the identified features in the acquired MRI data, monitoring spatial and temporal progress of HIFU-histotripsy-induced mechanical fractionation of the biological material within the target volume.

In yet one more respect, the invention provides a non-transitory computer readable medium having stored thereon instructions that, upon execution by one or more processors of an apparatus, cause the apparatus to carry out operations, wherein the apparatus comprises a high-intensity focused ultrasound (HIFU) histotripsy subsystem and a magnetic resonance imaging (MRI) subsystem, and wherein the operations include: applying HIFU histotripsy to a mass of biological material in order to mechanically fractionate a target volume of biological material within the mass; concurrently with applying the HIFU histotripsy to the mass of biological material, acquiring with the MRI subsystem one or more magnetic resonance (MR) mechanical-metric renderings of the mass of biological material in a region including the target volume; identifying in at least one of the one or more acquired MR mechanical-metric renderings features corresponding to HIFU-histotripsy-induced displacement of the biological material within the mass; and based on the identified features in the at least one of the one or more acquired MR mechanical-metric renderings, monitoring a spatial location within the mass of biological material of a focal point of the HIFU histotripsy.

In still one more respect, the invention provides a non-transitory computer readable medium having stored thereon instructions that, upon execution by one or more processors of an apparatus, cause the apparatus to carry out operations, wherein the apparatus comprises a high-intensity focused ultrasound (HIFU) histotripsy subsystem and a magnetic resonance imaging (MRI) subsystem, and wherein the operations include: applying HIFU histotripsy to a mass of biological material in order to mechanically fractionate a target volume of the biological material within the mass; subsequent to applying the HIFU histotripsy to the mass of biological material, acquiring MRI data of the mass of biological material in a region including the target volume; identifying in the acquired MRI data features corresponding to HIFU-histotripsy-induced mechanical fractionation of the biological material within the mass; and based on the identified features in the acquired MRI data, determining a location and a spatial extent of HIFU-histotripsy-induced mechanical fractionation of the biological material within the target volume.

These as well as other aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrate the invention by way of example only and, as such, that numerous variations are possible.

BRIEF DESCRIPTION OF DRAWINGS

FIG. 9A shows a sagittal-plane view of real-time MR temperature mapping of ultrasonic mechanical fractionation of a volume within an ex vivo bovine liver, in accordance with example embodiments.

FIG. 12A shows a coronal-plane view of a real-time MR temperature map during ultrasonic mechanical fractionation of a volume within an ex vivo bovine liver, in accordance with example embodiments.

FIG. 12B shows a sagittal-plane view of a real-time MR temperature map during ultrasonic mechanical fractionation of a volume within an ex vivo bovine liver, in accordance with example embodiments.

FIG. 12C shows a real-time MR temperature curve as a function of time during ultrasonic mechanical fractionation of a volume within an ex vivo bovine liver, in accordance with example embodiments.

FIG. 12D shows a coronal-plane view of real-time MR magnitude image during ultrasonic mechanical fractionation of a volume within an ex vivo bovine liver, in accordance with example embodiments.

FIG. 12E shows a sagittal-plane view of a real-time MR magnitude image during ultrasonic mechanical fractionation of a volume within an ex vivo bovine liver, in accordance with example embodiments.

FIG. 12F shows a coronal-plane view of a MR magnitude image of an ex vivo bovine liver following ultrasonic mechanical fractionation of four objects, in accordance with example embodiments.

FIG. 13A shows a coronal-plane view of a real-time MR temperature map during ultrasonic thermal ablation of a volume within an ex vivo bovine liver.

FIG. 13B shows a sagittal-plane view of a real-time MR temperature map during ultrasonic thermal ablation of a volume within an ex vivo bovine liver.

FIG. 13C shows a real-time MR temperature curve as a function of time during ultrasonic thermal ablation of a volume within an ex vivo bovine liver.

FIG. 13D shows a coronal-plane view of a MR magnitude image of an ex vivo bovine liver after multiple (4) volumetric ultrasonic mechanical fractionations followed by thermal ablation in the center (not visible).

FIG. 14A shows an MR T2-weighted image of ultrasonic mechanical fractionation of a volume within an ex vivo bovine liver following sonications using four different duty factors as well as one thermal ablation, in accordance with example embodiments.

FIG. 14B shows an MR T1-weighted image of ultrasonic mechanical fractionation of a volume within an ex vivo bovine liver following sonications using four different duty factors as well as one thermal ablation, in accordance with example embodiments.

DETAILED DESCRIPTION

1. Overview

Figure 1:
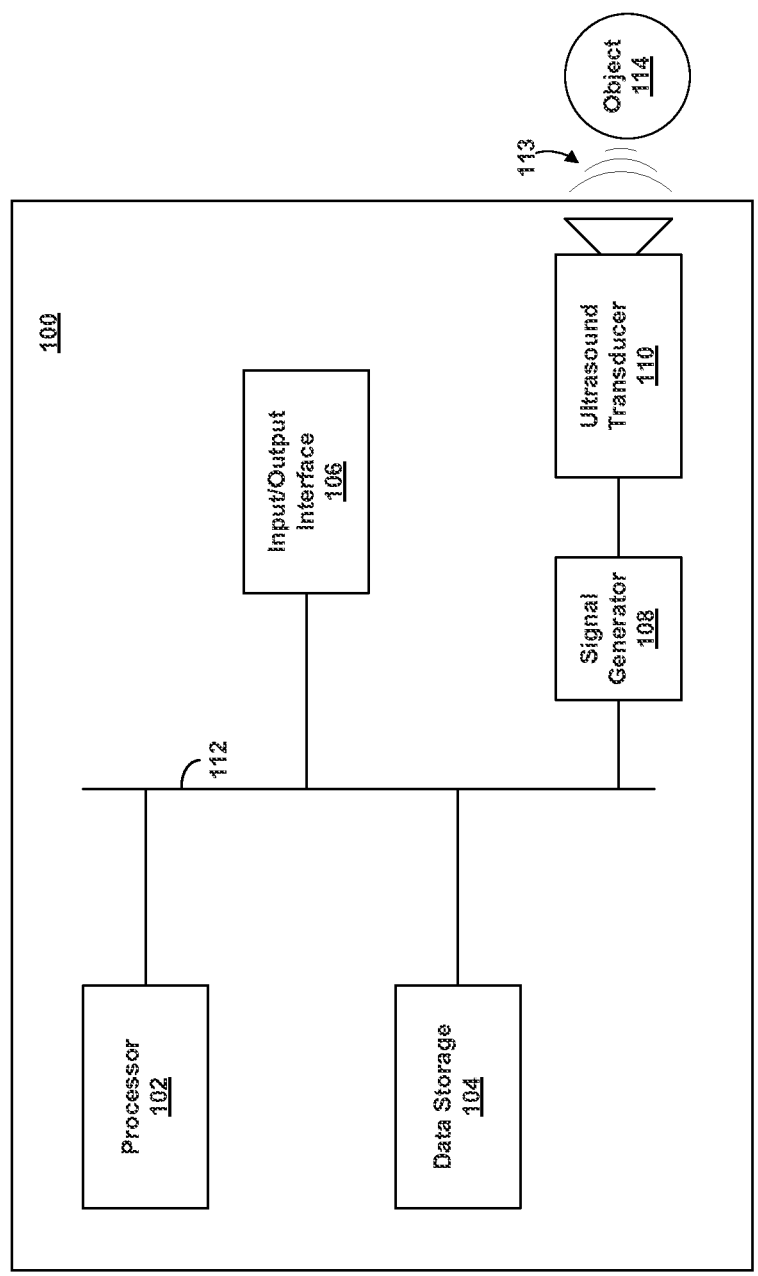
FIG. 1 is a simplified block diagram of a system configured for ultrasonic mechanical fractionation of a volume within an object, in accordance with example embodiments.

Although magnetic resonance imaging (MRI) and related MR diagnostic techniques are important aspects of HIFU therapy, the purely thermal nature of conventional HIFU can limit the utility of MRI and MR techniques for monitoring, control and diagnostic evaluation of HIFU when applied clinically or even experimentally. The limitations are largely due to heat delivery by diffusion within a target region of biological material (e.g., biological tissue) undergoing HIFU sonication. In particular, when one or another form of biological material is subjected to HIFU sonication, diffusion of absorbed heat outward from a focal point of the high intensity ultrasound sonication renders lesion formation somewhat imprecise and/or unpredictable. For example, the boundary between thermally ablated biological material in the immediate vicinity of the focus and undisturbed (e.g., intact) material further from the focus may move outward the sonicated volume. And, the boundary itself may lack sharpness, forming instead a zone of relatively gradual transition from fully ablated material (e.g., within a lesion) to undisturbed material surrounding the ablated material.

One result of the somewhat imprecise nature of HIFU-induced lesion formation in biological material is a correspondingly imprecise ability to monitor and control lesion formation using HIFU in the first place. Another result is that MRI and MR techniques used in conjunction with HIFU for the purpose of control and evaluation of results can themselves be limited by gradation of contrast changes across lesion boundaries, for example. This, in turn, may diminish the evaluative utility of MR data acquired during and/or after HIFU sonication. Furthermore, the time interval over which heat absorbed by biological material during HIFU sonication dissipates may extend somewhat beyond that over which HIFU sonication is actually applied. Consequently, the volumetric extent of lesion formation may not be known until some instant after HIFU sonication ceases. This can limit the utility of MRI and MR techniques for real-time monitoring of the effects of HIFU during sonication; the viability evaluating the final lesion size may be similarly constrained.

Accordingly, there is a need for techniques that integrate precise and efficacious monitoring, control, and evaluation into HIFU-based targeted destruction of biological material.

Disclosed herein are a method and system for employing a novel adaptation of conventional HIFU that provides for significantly more control and precision in targeted HIFU-induced destruction of biological material, and that is carried out in conjunction with a high degree of precise MR-based monitoring, control, and evaluation of the targeted, therapeutic destruction process. In accordance with example embodiments, HIFU is adapted to devise a technique that can cause targeted and controlled destruction of biological material by mechanical fractionation instead by purely diffuse heat ablation. Using this mechanical fractionation technique enables controlled destruction within a target region of biological material to be significantly more precise in volumetric extent, physical boundary definition, and post-sonication heat dissipation than can typically be achieved with pure ablation from conventional HIFU. Also in accordance with example embodiments, MRI and MR methods can be carried out in conjunction with the mechanical fractionation technique to yield much more precise monitoring, control, and post-treatment evaluation of sonicated regions than can be obtained by MRI and MR methods applied in conventional HIFU.

In an example embodiment, an adapted HIFU technique termed "boiling histotripsy" (BH) is used for generating mechanically fractionated lesions in biological material, such as biological tissue. BH is a therapeutic technique in which mechanically fractionated lesions can be purely mechanical in origin, i.e. liquefied, or include different degrees of thermal damage controlled by the parameters of an ultrasound exposure (sonication) protocol [2, 3]. Specifically, the peak output power, in situ shock amplitude, ultrasound frequency, pulse length, pulse repetition rate, number of pulses, and sonication trajectory can be adjusted.

In one example demonstration, BH sonication was performed volumetrically, i.e., concurrently or sequentially heating regions larger than a single focal point. This work has been described in U.S. Provisional Application No. 61/972,035, which is incorporated by reference herein in its entirety. In another example demonstration, various MRI methods were used to monitor BH sonication in real-time, as well as assess the therapy outcome. This further work has been described in U.S. Provisional Application No. 61/971,432.

MRI can provide in vivo anatomical, functional, and temperature images, as well as provide information on, e.g., tissue displacement in real time during a HIFU sonication. While volumetric, MRI-based feedback can be used to control conventional MR-HIFU thermal ablation, (e.g., to achieve complete thermal necrosis in the target region), as well as to control conventional MR-HIFU mediated mild hyperthermia, these techniques rely on the monitoring of HIFU-induced temperature changes only [1].

The BH method can be used to induce mechanically-fractionated lesions with a controlled degree of thermal effect [3, 4]. The technique utilizes repetitive millisecond-long pulses with shocks, rapid boiling in tissue (or more generally, biological material) caused by shock wave heating, and interaction of shocks with a vapor cavity [5]. Such an approach can be advantageous for a number of clinical applications where it is necessary to avoid overheating vessels, bone, or other structures located close to the treatment site, as well as to accelerate resorption or passage of the ablated tissue volume, diminish pressure on the surrounding organs that causes discomfort, and insert openings between tissues, among other desired and/or required effects or outcomes.

One of the benefits enabled by BH is the ability to use MRI to accurately plan BH-sonications, to perform BH-therapy under real-time imaging guidance, and evaluate the outcome of the treatment [6].

A thermally coagulated region is estimated based on accumulated thermal dose, and may not accurately reflect the final post-therapy outcome. Similarly, in mild hyperthermia, temperature in the target region is elevated to 40-45 C for a prolonged duration, after which the tissue is allowed to cool down. The region of mild hyperthermia is estimated from the temperature gradients and/or thermal dose over time. However, during neither of thermal ablation or mild hyperthermia are tissue contrast changes typically seen in real time MR-imaging.

In contrast, various MRI methods can be used during the BH-mediated mechanical tissue fractionation to monitor progress of BH in real time, based on tissue contrast changes. Consequently, the therapy may also be controlled using an MR-based monitoring. For example, during BH therapy, real-time imaging findings can provide a basis for adjusting the sonication power, duty cycle, duration, number of pulses, and sonication trajectory for optimum results (e.g., full mechanical fractionation of tissue at the target location). In addition to monitoring contrast changes in real time, temperature can be monitored simultaneously within and outside of the target region, and used as an additional feedback method in order to, avoid high temperatures at the target as well as avoid temperature elevations and tissue damage outside of the target region, for example. Use of MRI and MR techniques in conjunction with BH (and HIFU histotripsy in general) to plan, monitor, control, and evaluate BH-induced targeted destruction of biological material prior to, during, and after BH sonication is referred to herein as "MRI-assisted BH."

The term "biological material" (and the like) is used herein to refer generically to material such as human (or other animal) tissue and/or organs, as well as other material of biological origin. Biological tissue (human or other) can be part of a living or non-living subject. For example, in some of the discussions below, demonstration operations of MRI-assisted BH were applied to sample biological material including ex vivo bovine liver and heart. Other, non-limiting examples of "biological material" used herein include biological tissue, such as liver tissue, uterine tissue, kidney tissue, prostate tissue, thyroid tissue, pancreas tissue, brain tissue, nerve tissue, connective tissue, or muscle tissue. Biological material can also include a biological substance, such as a blood clot or a hematoma.

The terminology "targeted destruction of biological material" (and the like) used herein is generally synonymous with controlled and/or intentional lesion formation in tissue and/or organs, although the result of such intentional "destruction of biological material" may not necessarily be a lesion. As conventional HIFU thermal ablation methods have been used successfully in the treatment of a range of tumors in different organs, including liver, uterus, kidney, and prostate, it can be anticipated with confidence that MRI-assisted BH techniques described herein by way of example embodiments can also be successfully applied in therapeutic treatment of tissue and/or organs of living humans (and other animals). Further, MRI-assisted BH can be applied to treatment of pathological tissue, such as malignant tumors and/or benign tumor, where non-limiting examples of benign tumors include an adenoma or a fibroid. Additionally, MRI-assisted BH can used to create and/or insert of openings in biological tissue for various therapeutic purposes.

It should be noted that various changes and modifications to the presently preferred embodiments described herein will be apparent to those skilled in the art. Such changes and modifications may be made without departing from the spirit and scope of the present invention and without diminishing its attendant advantages.

2. Histotripsy

As noted above, a conventional HIFU wave having a power density of less than 1 kW/cm$^2$ can be sequentially focused upon various portions of an object so that a relatively large region of the object is thermally ablated. HIFU boiling histotripsy utilizing HIFU waves having power density of at least 10 kW/cm$^2$ is also useful for mechanical ablation of small portions of an object, but has previously not been used to mechanically ablate regions that are substantially larger than a focal point of the HIFU wave. These currently known HIFU methods for thermal or mechanical ablation suffer from disadvantages that are discussed below.

Using HIFU waves to predictably and uniformly thermally ablate a relatively large region of an object may require process downtime between ablation of successive portions of the object. The process downtime allows recently ablated portions of the object to cool before ablation of a successive portion begins. Causing thermal ablation of successive portions of the object without allowing for cooling of recently ablated portions may introduce non-uniformity and unpredictability to the ablation process.

More specifically, uniform thermal ablation of two portions of an object generally requires that the two portions experience the same absorbed HIFU power density for the same continuous duration, starting from the same initial temperature. This combination of absorbed HIFU power, exposure time, and initial temperature is sometimes referred to as a HIFU "thermal dose." However, if the two portions are adjacent, heat generated in ablating the first portion may diffuse into the second portion, raising the temperature of the second portion before the second portion receives its predetermined HIFU dose. This will generally cause the second portion to absorb more heat than the first portion, unless the HIFU dose for the second portion is appropriately compensated. However, it is difficult to accurately determine how much surplus heat the second portion absorbs while the first portion is being ablated. Therefore, it is usually desirable to give each portion of the object an equal "thermal dose" of the HIFU wave, while allowing time for sufficient cooling between ablating each portion. The process downtime represented by such cooling time periods makes the ablation process somewhat inefficient.

The effectiveness of HIFU boiling histotripsy in uniformly mechanically ablating a relatively large region of an object has been previously unknown. The methods disclosed herein exhibit uniform mechanical ablation of a relatively large region of an object without the need for process downtime related to cooling of ablated portions of the object. HIFU intensities used in the disclosed methods are high enough to generate shock waves at or near the focal point of the HIFU wave. The shock waves then cause a portion of the object to boil, which in turn generates a vapor cavity. The shock wave interacts with the vapor cavity to cause mechanical ablation of the portion of the object. Unexpectedly, the disclosed methods have advantages that differ from previously known methods in the following ways.

First, uniform ablation of two portions of an object no longer requires the continuity of the receiving a required number of pulses to generate mechanical ablation of each of them. Using the disclosed methods, two portions can be uniformly ablated even though the two portions receive the required number of HIFU pulses that differ in continuity. For example, uniform ablation of first and second portions could result from sending HIFU pulses of 10 ms and 1% duty cycle and 80 MPa shock amplitude in the following sequence: the first portion receiving one HIFU pulse and then the second portion receiving one HIFU pulse. The process is then repeated the necessary number of times. In another example, uniform ablation of the first and second portions could result from the first portion receiving all necessary number of pulses and then the second portion receiving a necessary number of pulses. Because the disclosed methods are primarily mechanical and not thermal processes, temperature history of each portion is largely irrelevant in this context.

On a related note, the primarily mechanical nature of the disclosed methods means that ablation of a first portion generally has little effect on a second portion. Short bursts of HIFU waves having a power density of at least 10 kW/cm$^2$ have been shown to generally affect only the portion of the object impacted by the HIFU wave and not surrounding portions.

Referring now to the Figures, FIG. 1 illustrates an example system 100 configured to ablate an object 114 using an acoustic ultrasound wave (or "HIFU" wave) 113. The system 100 includes a processor 102, data storage 104, an input/output interface 106, a signal generator 108, and an ultrasound transducer 110, any or all of which may be communicatively coupled to each other via a system bus or another connection mechanism 112.

The processor 102 may include a general purpose processor and/or a special purpose processor and may be configured to execute program instructions stored within data storage 104. In some examples, the processor 102 may be a multi-core processor comprised of one or more processing units configured to coordinate to execute instructions stored within data storage 104. In one example, the processor 102, by executing program instructions stored within data storage 104, may provide HIFU parameters to the signal generator 108 for generation of HIFU waves. In another example, the processor 102 may provide HIFU parameters that are received via the input/output interface 106 to the signal generator 108.

Data storage 104 may include one or more volatile, non-volatile, removable, and/or non-removable storage components. Data storage 104 may be a magnetic, optical, or flash storage medium, and may be integrated in whole or in part with the processor 102 or other portions of the system 100. Further, the data storage 104 may be a non-transitory computer-readable storage medium, having stored thereon program instructions that, when executed by the processor 102, cause the system 100 to perform one or more functions described in this disclosure. Such program instructions may be part of a software application that can be executed in response to inputs received from the input/output interface 106, for instance. The data storage 104 may also store other types of information or data, such as those types described throughout this disclosure.

The input/output interface 106 may enable interaction with a user of the system 100, if applicable. The input/output interface 106 may include input components such as a keyboard, a mouse, a keypad, or a touch-sensitive panel, and output components such as a display screen (which, for example, may be combined with a touch-sensitive panel), a sound speaker, and a haptic feedback system. In one example, the input/output interface 106 may receive input indicating various parameters for a HIFU wave to be generated by the ultrasound transducer 110.

The signal generator 108 may be configured to receive data from the processor 102 indicative of HIFU parameters for generation of a HIFU wave by the ultrasound transducer 110. For example, the processor 102 may send, to the signal generator 108, data representative of input received via the input/output interface 106. In another example, the received input may simply indicate one of several predetermined HIFU ablation protocols represented by program instructions stored at data storage 104. Such data received by the signal generator 108 may indicate various HIFU parameters such as power, power density, oscillation frequency, pulse duration, duty cycle, and a number of pulses to be generated for various portions of the object 114. The received data may also indicate a trajectory, path, or sequence of portions of the object 114 upon which the focal point of the HIFU wave should be sequentially directed upon. The received data may also include timing information indicating when and/or for how long the focal point of the HIFU wave should be directed upon each respective portion of the object 114.

The ultrasound transducer 110 may include one or more piezoelectric transducer elements configured to generate HIFU waves in response to receiving respective control signals representing HIFU parameters from the signal generator 108. For example, the ultrasound transducer 110 may include a phased array of transducer elements configured to electronically focus or steer a generated HIFU wave upon various portions of the object 114 via constructive and/or destructive wave interference. Each transducer element of the ultrasound transducer 110 may receive its own independent control signal from the signal generator 108. In some examples, the signal generator 108 and the ultrasound transducer 110 may be integrated into one functional unit. The ultrasound transducer 110 may include one or more of (i) a lens, (ii) one or more transducers having a radius of curvature at the focal point of the HIFU wave, and (iii) a phased array of transducers.

The object 114 may include any object suitable for HIFU ablation. Some examples of an object 114 include biological tissue such as a tumor, a hematoma, an abscess, a lipoma, or any other diseased or undesirable tissue.

Figure 2:
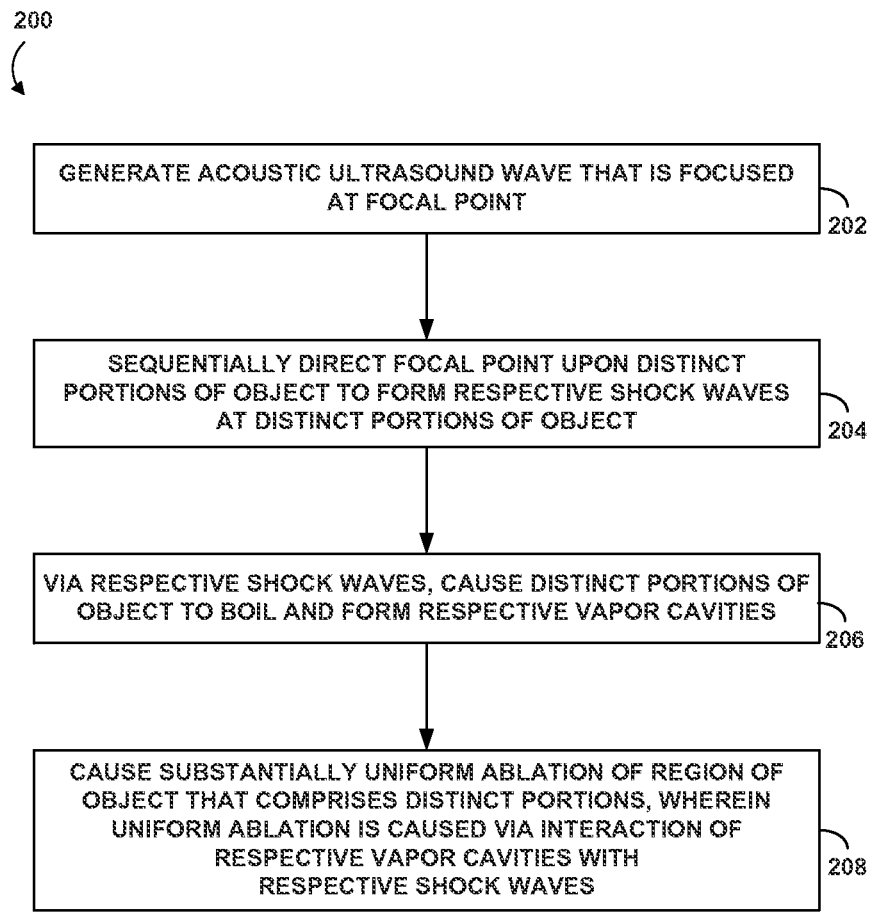
FIG. 2 is a flow chart depicting an example method for ultrasonic mechanical fractionation of a volume within an object, in accordance with example embodiments.

FIG. 2 is a flow chart depicting an example method 200 for causing substantially uniform ablation of a region of an object that comprises distinct portions. At block 202, the method 200 involves generating an acoustic ultrasound wave that is focused at a focal point. Hereinafter, the acoustic ultrasound wave may also be referred to as the HIFU wave.

The HIFU wave may be generated by system 100 according to one or more parameters received via input/output interface 106 and/or stored at data storage 104. Such parameters that define characteristics of the generated HIFU wave may include peak power, ultrasound frequency, pulse duration, duty cycle, shock amplitude in the focal waveform, and a number of pulses to be radiated to a given portion of the object 114. The HIFU wave may be focused at the focal point defined by the geometry of the ultrasound transducer 110, and/or focused electronically via providing appropriate respective control signals to a phased array of transducer elements of the ultrasound transducer 110. The HIFU wave may be generated by the ultrasound transducer 110 via one or more of a lens or one or more transducers having a radius of curvature at the focal point. The focal point of the HIFU wave may resemble a zero-dimensional point, or in other examples, the focal point may resemble a three-dimensional focal volume.

Figure 3:
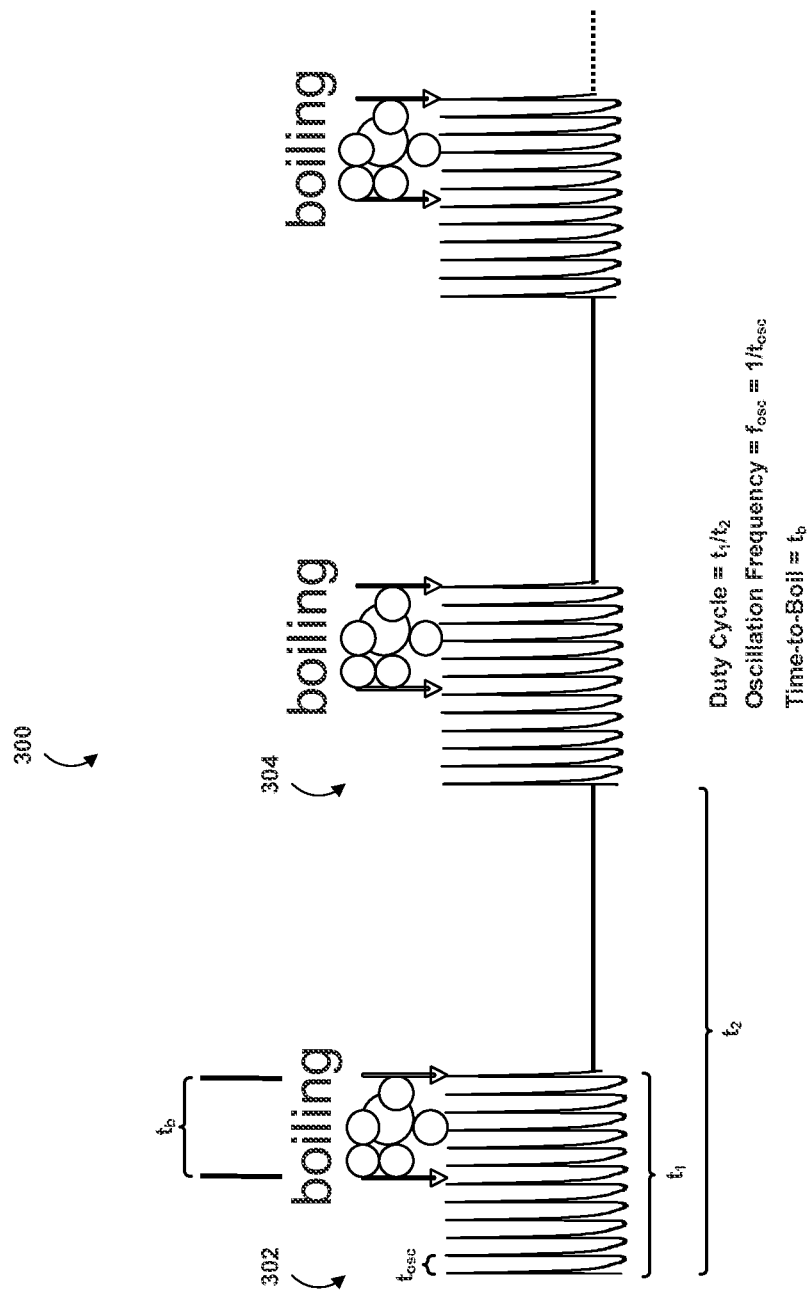
FIG. 3 is depicts a waveform representing an example acoustic ultrasound wave generated by a system configured for ultrasonic mechanical fractionation of a volume within an object, in accordance with example embodiments.

Various HIFU wave parameters described below may be useful for causing substantially uniform ablation of a macroscopic region of an object. In some examples, the HIFU wave has an oscillation frequency that is greater than 900 kHz and less than 10 MHz. More specifically, the HIFU wave may have an oscillation frequency of about 1.2 MHz. Referring to FIG. 3 as an example, the HIFU wave 300 may exhibit an oscillation frequency $f_{osc}$=1.2 MHz that corresponds to an oscillation period of $t_{osc}$=0.833 μs.

The HIFU wave 300 may also exhibit a duty cycle ($t_1/t_2$) that represents a ratio of a pulse duration $t_1$ during which the HIFU wave 300 has a non-zero amplitude, over a time $t_2$ that elapses between the respective starts of consecutive pulses 302 and 304 of the HIFU wave 300. In some examples, the HIFU wave 300 has a duty cycle that is greater than 0.005 and less than 0.12. More specifically, the HIFU wave 300 may have a duty cycle of about 0.01. Such relatively short duty cycles may limit an amount of heat that is allowed to accumulate within the object 114 during ablation.

In some examples, the HIFU wave 300 has a pulse duration $t_1$ that is greater than 1 millisecond (ms) and less than or equal to 40 ms. More specifically, the HIFU wave may have a pulse duration that is less than or equal to 20 ms, or about 10 ms. For example, the HIFU wave 300 may have a pulse duration of $t_1$=10 ms and a pulse repetition period of $t_2$=1 second, resulting in a duty cycle of 0.01. Note that with respect to any examples described herein, HIFU wave 300 might not be shown to scale in FIG. 3.

In some examples, the HIFU wave 300 has a shock front larger than 40 MPa. More specifically, the HIFU wave may have a shock front that is higher than or equal to 80 MPa, or about 100 MPa. For example, the HIFU wave 300 may have a shock front that is higher than or equal to 80 MPa, or about 80 MPa.

As discussed below, a HIFU wave defined by certain parameters may induce boiling of a given portion the object within a time period $t_b$ of about 2 ms. The pulse duration $t_1$ may advantageously be somewhat longer than a time required to bring the given portion to a boil so that the shock fronts of the rest of the pulse interact with the vapor cavity resulting from boiling. Likewise, the duty cycle of the HIFU wave should be low enough so that substantial amounts of heat do not accumulate and diffuse into other portions of the object 114.

At block 204, the method 200 involves sequentially directing the focal point upon distinct portions of an object to form respective shock waves at the distinct portions of the object. The object may include the object 114. In some examples, a shock wave formed at a portion of the object may have a pressure magnitude of at least about 40 MPa at a focus of the shock wave. 40 MPa may be an approximate pressure amplitude necessary to cause boiling within the object within a few milliseconds.

In some examples, the focal point of the HIFU wave may be sequentially directed upon portions of the object that are each at least 0.5 millimeters (mm) long and no greater than 7 mm long. In further examples, the focal point of the HIFU wave may be sequentially directed upon portions of the object each having an area of at least 7 square millimeters (mm$^2$) and no greater than 30 mm$^2$. More specifically, each portion may have an area of about 15 mm$^2$.

The focal point of the HIFU wave may be sequentially directed upon portions of the object that as a whole have a total length of at least 1 centimeter (cm), a total area of at least 1 square centimeter (cm$^2$), and/or a total volume of at least 1 cubic centimeter (cm$^3$). In this way, the focal point of the HIFU wave can be directed across several relatively small portions of the object to ablate a larger macroscopic region of the object, as discussed further below.

Figure 4A:
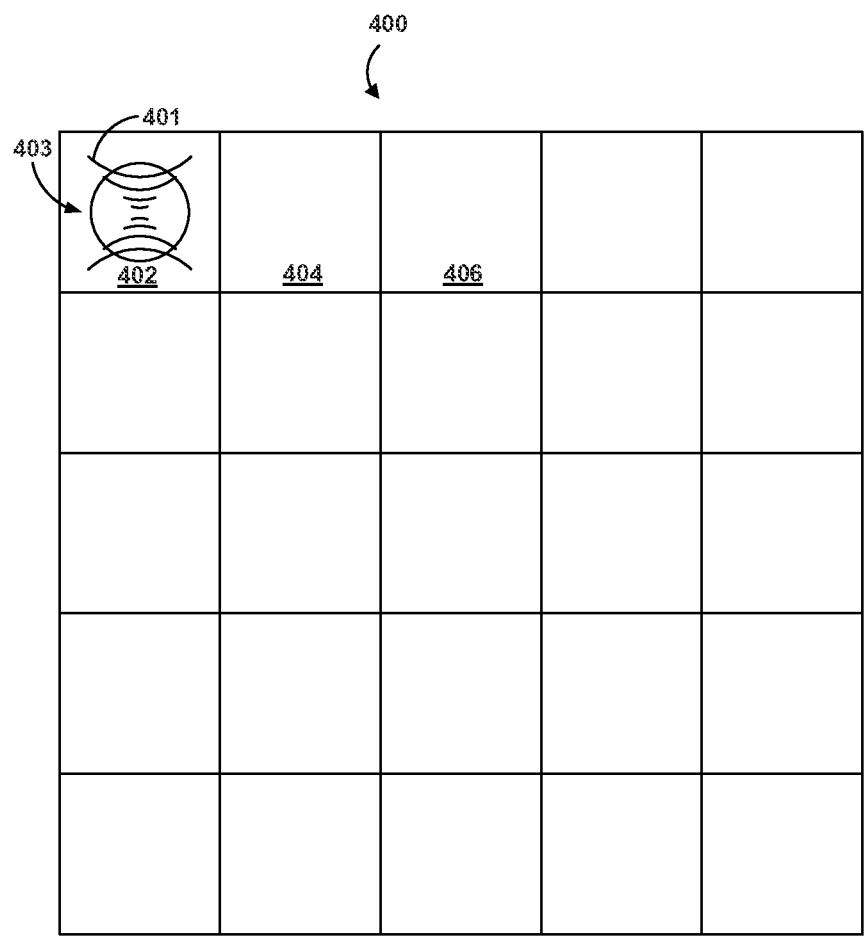
FIG. 4A is a conceptual illustration of ultrasonic mechanical fractionation of a first portion an example object, in accordance with example embodiments.
Figure 4B:
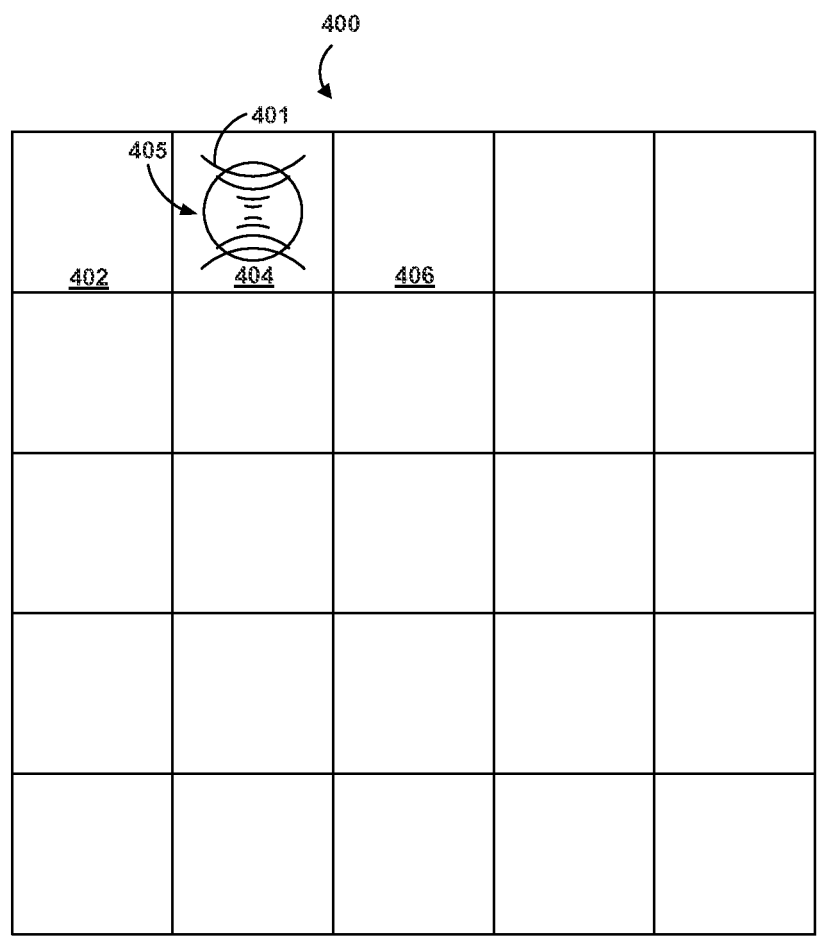
FIG. 4B is a conceptual illustration of ultrasonic mechanical fractionation of a second portion an example object, following ultrasonic mechanical fractionation of a first portion the example object, in accordance with example embodiments.
Figure 4C:
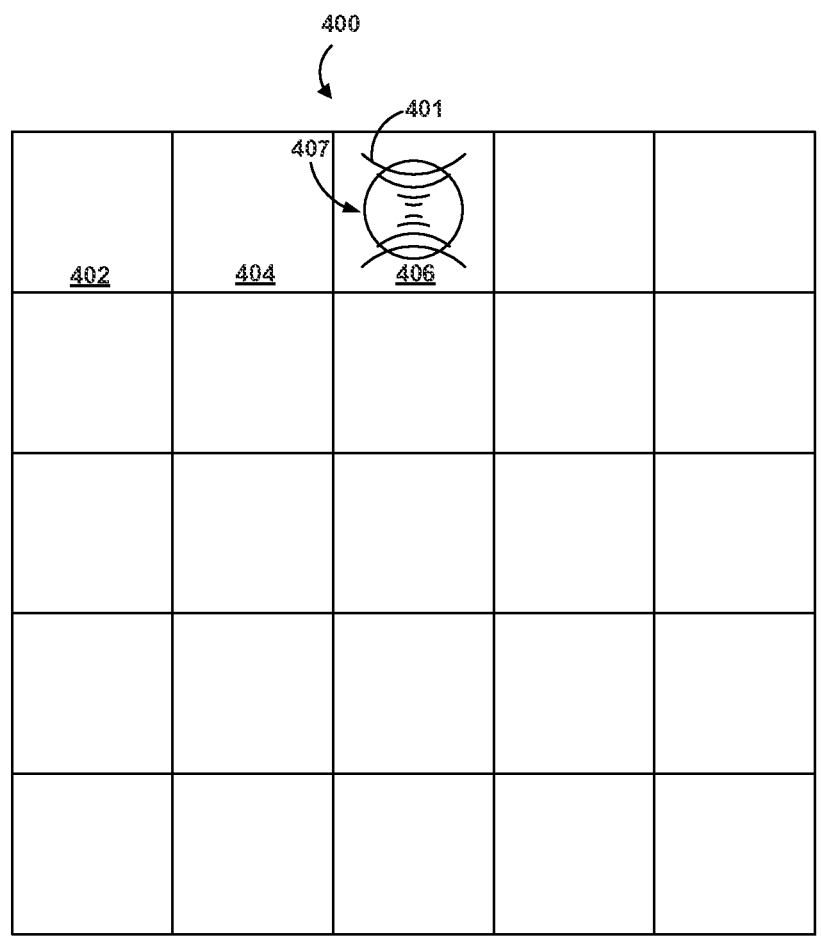
FIG. 4C is a conceptual illustration of ultrasonic mechanical fractionation of a third portion an example object, following ultrasonic mechanical fractionation of first and second portions the example object, in accordance with example embodiments.

In one example, the focal point of the HIFU wave 401 may be sequentially focused first upon portion 402 of the object 400 as shown in FIG. 4A, then upon portion 404 of the object 400 as shown in FIG. 4B, and then upon portion 406 of the object 400 as shown in FIG. 4C. This may result in shock waves being sequentially formed at the portions 402, 404, and 406. Other example trajectories or sequences for direction of the focal point of the HIFU wave 401 along various portions of the object 400 are also possible.

Figure 5:
FIG. 5 is a conceptual illustration of an array of distinct portions of an example object, in accordance with example embodiments.

FIG. 5 depicts an example object 500 for the purpose of illustrating other example sequences or trajectories that a focal point of a HIFU wave could be directed along. A first example trajectory could include sequentially focusing the focal point upon horizontal portions of the object. Such an example trajectory is depicted as the sequence 502, 504, 506, 508, 510, 512, 514, 516, 518, 520, 522, 524, 526, 528, 530, 532, 534, 536, 538, 540, 542, 544, 546, 548, and 550. Another trajectory could include sequentially directing the focal point of the HIFU wave upon the portions of the object as defined by the sequence 502, 506, 510, 514, 518, 522, 526, 530, 534, 538, 542, 546, 550, 504, 508, 512, 516, 520, 524, 528, 532, 536, 540, 544, and 548. Yet another trajectory could include a spiral-like sequence 502, 504, 506, 508, 510, 520, 530, 540, 550, 548, 546, 544, 542, 532, 522, 512, 514, 516, 518, 528, 538, 536, 534, 524, and 526.

Numerous other trajectories or sequences are also possible. For example, the distinct portions of the object may form a closed loop, one or more concentric spheres, or one or more concentric circles. The distinct portions may all lie within a common line and/or a common plane. That is to say that the distinct portions of the object may define a line, an area, or a volume.

In some examples, the method 200 may further involve determining a trajectory of the distinct portions of the object such that distances between successive portions of the trajectory are maximized. In this context, sequentially directing the focal point upon the distinct portions of the object may include directing the focal point upon the distinct portions of the object according to the determined trajectory.

Sequentially directing the focal point upon the distinct portions of the object may also include determining how many pulses of the HIFU wave a given portion of the object should absorb before the focal point is redirected to another portion of the object. For example, the given portion may receive a number of pulses greater than 5 and less than about 180. More specifically, the given number of pulses may be about 30. The given number of pulses may roughly represent the number of pulses required for effective mechanical ablation of the given portion. For example, a first portion may receive a certain number of HIFU pulses, fully ablating the first portion, and then the focal point of the HIFU wave may be redirected to a second portion so that the second portion may be ablated.

In other examples, the given number of pulses might not be provided to the first portion all in one continuous session. That is, the focal point of the HIFU wave may be directed upon the first portion for receiving a partial number of HIFU pulses, then directed upon a second portion for receiving a full or partial number of HIFU pulses, and then redirected back to the first portion for receiving the remainder number of HIFU pulses.

At block 206, the method 200 involves, via the respective shock waves, causing the distinct portions of the object to boil and form respective vapor cavities. The HIFU wave 401 may experience non-linear propagation through the object 400 and become a shock wave near the center of portion 402, which in turn causes boiling within the portion 402. In some examples, the volume of the portion 402 heated to boiling may be greater than 0.1 cubic millimeters (mm$^3$) and less than 0.3 mm$^3$. The boiling causes a vapor cavity 403 to be formed within the portion 402. Generally, the portion 402 assumes a vapor state within the vapor cavity 403 and a liquid or solid form outside of the vapor cavity 403.

FIG. 4B depicts the HIFU wave 401 forming a shock wave near the center of portion 404, which in turn causes boiling within the portion 404. In some examples, the volume of the portion 404 heated to boiling temperature may greater than 0.1 mm$^3$ and less than 0.3 mm$^3$. The boiling causes a vapor cavity 405 to be formed within the portion 404. Generally, the portion 404 assumes a vapor state within the vapor cavity 405 and a liquid or solid form outside of the vapor cavity 405. FIG. 4B depicts portion 402 as an ablated void within the object 400. This will be further discussed below.

In a similar fashion, FIG. 4C depicts the HIFU wave 401 forming a shock wave near the center of portion 406, which in turn causes boiling within the portion 406. In some examples, the volume of the portion 406 heated to boiling temperature may be greater than 0.1 mm$^3$ and less than 0.3 mm$^3$. The boiling causes a vapor cavity 407 to be formed within the portion 406. Generally, the portion 406 assumes a vapor state within the vapor cavity 407 and a liquid or solid form outside of the vapor cavity 407. FIG. 4C depicts portion 404 as an ablated void within the object 400. This will be further discussed below.

At block 208, the method 200 involves causing substantially uniform ablation of a region of the object that comprises the distinct portions. The substantially uniform ablation is caused via interaction of the respective vapor cavities with the respective shock waves.

As shown in FIG. 4A, interaction of the vapor cavity 403 and the shock wave induced by HIFU wave 401 has ablated portion 402 of the object 400. For example, the shock wave near the center of portion 402 may interact with the boundary of the growing vapor cavity 403 to ablate the portion 402. The shock wave may cause tissue disintegration at the boundary of the vapor cavity 403 due to the vapor/solid discontinuity or the vapor/liquid discontinuity at the boundary. The vapor cavity 403 grows in size as more of the portion 402 is induced to boil and interaction of the shock wave with the vapor cavity 403 cause tissue disintegration of the portion 402 of the object.

As similarly shown in FIGS. 4B and 4C, interaction of the vapor cavities 405 and and 407 with the shock wave induced by HIFU wave 401 has ablated portions 404 and 406 of the object 400. For example, the shock wave near the center of portion 404 may interact with the boundary of the growing vapor cavity 405 to ablate the portion 404. The shock wave may preferentially interact with the boundary of the vapor cavity 405 due to the vapor/solid discontinuity or the vapor/liquid discontinuity at the boundary. The vapor cavity 405 grows in size as more of the portion 404 is induced to boil and interaction of the shock wave with the vapor cavity 403 cause tissue disintegration of the portion 404 of the object. As a result, both portions 402 and 404 are substantially uniformly ablated.

In some examples, both portions 402 and 404 are liquefied and removed from the object 400 to create a void. Each time the HIFU wave 401 is focused upon a new portion of the object, the HIFU wave may cause a new liquefied volume to form within the new portion of the object. Such a liquefied volume may be greater than about 1 mm$^3$ and less than about 10 mm$^3$.

In some examples, boiling of the respective portions of the object 400 may cause pure mechanical ablation (i.e., liquification or liquefaction) and/or thermal ablation of various portions of the object. For example the uniform ablation methods disclosed herein may include a combination of thermal ablation and mechanical ablation of various portions of the object. Use of preferred parameters for the HIFU wave, however, will generally result in ablation that is primarily mechanical in nature and not thermal in nature. In one example where the object 400 is undesirable biological tissue, liquefied portions of the undesirable tissue may be flushed out of a patient's body via their lymphatic and/or cardiovascular system or drained using a needle.

Where the biological tissue is a tumor, the method may involve treating a subject having the tumor with an amount effective of the focused acoustic ultrasound wave to ablate all or a portion of the tumor.

Where the biological tissue is a hematoma, the method may involve treating a subject having the hematoma with an amount effective of the focused acoustic ultrasound wave to ablate all or a portion of the hematoma.

Where the biological tissue is an abscess, the method may involve treating a subject having the abscess with an amount effective of the focused acoustic ultrasound wave to ablate all or a portion of the abscess.

Where the biological tissue is a lipoma, the method may involve treating a subject having the lipoma with an amount effective of the focused acoustic ultrasound wave to ablate all or a portion of the lipoma.

Where the biological tissue is a diseased tissue, the method may involve treating a subject having the diseased tissue with an amount effective of the focused acoustic ultrasound wave to ablate all or a portion of the diseased tissue.

3. MRI-Assisted BH

MR-imaging methods for BH therapy using a clinical MR-HIFU system have been developed and characterized to aid in mitigating the possible risks associated with high instantaneous acoustic pressures in BH treatments. This includes accurate treatment planning, real-time multi-planar monitoring of the BH-lesion as well as temperature elevations during therapy, and visualization and quantification of the therapy outcome. In addition to monitoring lesion formation and temperature elevation in real time, MR image information can be also used as a basis for controlling or adjusting the treatment (e.g., closed or user-adjustable feedback-loop) so that the correct lesion location and volume is treated and that temperature elevation stays below the threshold for thermal damage both within and outside the target region. These MR-based monitoring methods can be adjusted to provide sufficient contrast of BH-lesions in most organs or target locations in vivo. They can be also applied to other HIFU methods aimed to mechanically fractionate tissue.

Accurate planning and targeting can be achieved using various MRI and MR-related techniques, either individually or in combination. Non-limiting examples of these techniques include T2-weighted, T1-weighted, T2 maps, T1 maps, T2* maps, and proton density weighted imaging. In addition, MR elastography (MRE) can be used to map tissue stiffness following sonication. Further, MR acoustic radiation force imaging (MR-ARFI) can be used during sonication to rapidly localize the HIFU focal point over one pulse or multiple pulses by capturing HIFU-induced tissue displacement in the MR image. Regions-of-interest (ROI) within the target region can be drawn on the planning images, based on which sonication trajectories are automatically calculated.

MR data acquired before, during, and after application of BH sonication of biological material can take various forms and can be represented and/or presented in various forms for viewing, analysis, and monitoring, and control. For purposes of the discussion herein, the terms "rendering," "renderings," "MR renderings," "MRI renderings" and the like will be used as a general reference to one or another of various forms in which MR data can be represented and/or presented. Non-limiting examples of MRI renderings include diffusion-weighted images, T1-weighted images, T2-weighted images, proton density-weighted images, T1 maps, T2 maps, T1*-weighted images, T2*-weighted images, T2* maps, T1-ρ-weighted images, fluid attenuated inversion recovery (FLAIR) images, susceptibility-weighted images (SWIs), diffusion maps, or a combined MRI rendering of at least two of the preceding renderings. Additional examples include MR "mechanical-metric renderings" that can be evaluated to indicate mechanical properties or characteristics of an object (e.g., biological material). Such renderings include magnetic resonance elastography (MRE) images, magnetic resonance acoustic radiation force images (MR-ARFIs), MR elasticity (stiffness) maps, and MR displacement maps. Further examples include MRI "thermal-metric maps," such as MRI temperature maps and thermal dose (e.g., equivalent minutes at 43° C. calculated from MRI temperature maps) maps.

4. Example System and Demonstration Results

A demonstration system for carrying out MR-assisted BH is described in [7]. The system includes a Philips Achieva 3T clinical MR scanner for acquiring MR data before, during, and after sonication, and a Philips Sonalleve clinical HIFU system. Transducer element driving signal phases were manipulated to perform volumetric sonications [8]. Peak acoustic power within a HIFU pulse, pulse repetition frequency, and pulse length were manipulated to perform BH-sonications with variable degree of thermal effect [4].

The Philips Achieva 3T clinical MR scanner was used for imaging. Different MR-imaging methods were used to plan the BH target locations, to perform real-time temperature mapping and BH lesion visualization, and to assess the therapy outcome and locations of BH lesions. Various demonstration runs were carried out, as described below.

Figure 6:
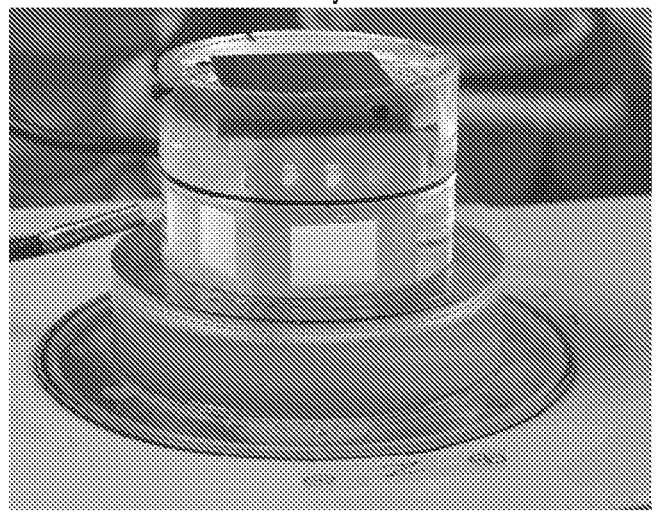
FIG. 6 depicts elements of a system for magnetic resonance image (MRI) monitoring of ultrasonic mechanical fractionation of a volume within an object, in accordance with example embodiments.
Figure 6:
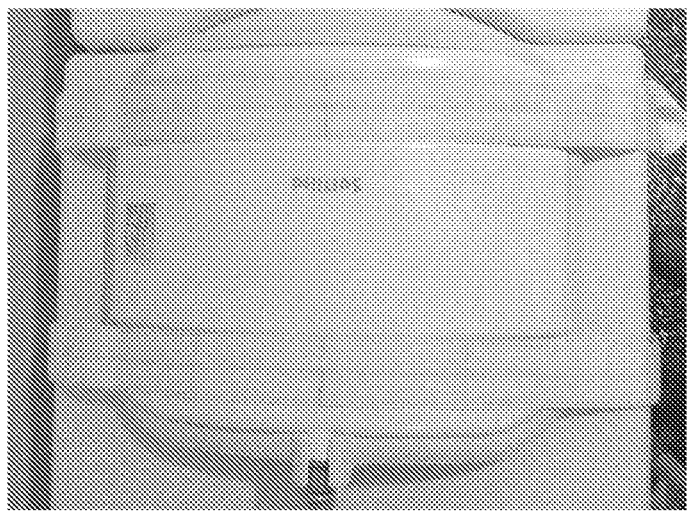
Figure 6:
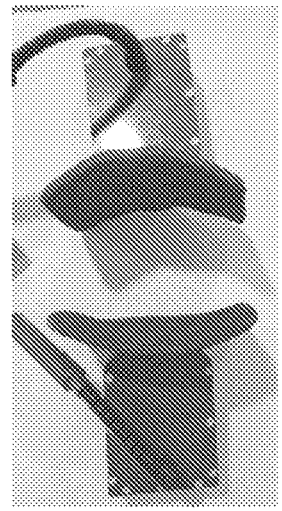

Demonstration runs were carried out on multiple samples of ex vivo bovine liver. Each sample had approximate linear dimensions of 6×6×4 cm. For the demonstration runs, a cylindrical water tank with a diameter of 20 cm was constructed to hold the samples. The form factor of the water tank sample holder was fashioned to allow it to fit into the MR scanner together with a posterior MR receive coil. In addition, a custom-built carotid MR coil was placed around the sample holder. FIG. 6 shows the sample holder, the posterior MR receive coil, and the carotid MR receive coil.

Figure 7:
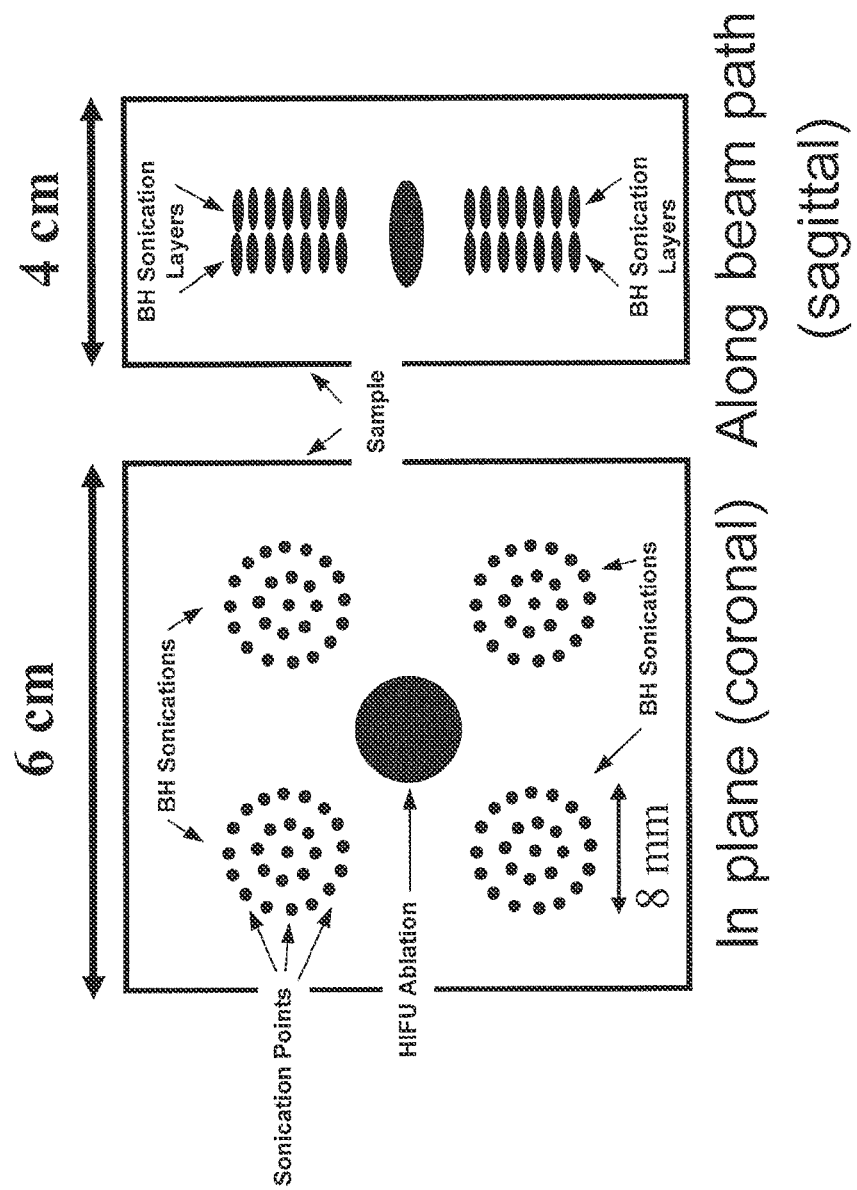
FIG. 7 is a conceptual illustration of a sonication protocol for ultrasonic mechanical fractionation of a volume within an example object, in accordance with example embodiments.

FIG. 7 is a conceptual illustration of the configuration of sonication for the demonstration runs. For each demonstration run, a sample was positioned such that its square 6×6 cm face was in the plane (parallel) to the coronal plane of the MR scanner, and its 4 cm depth was in the sagittal plane of the scanner. With this configuration, sonication was applied along the sagittal plane direction; i.e., normal to the square 6×6 cm face of each sample. A sonication protocol was used that applied four volumetric BH sonications arranged in four symmetric quadrants of the 6×6 cm face of each sample, and one volumetric HIFU thermal ablation for reference at the center of the 6×6 cm face. The four sonications were carried using pulse repetition frequencies (PRFs) of 1, 3, 5, and 10 Hz, respectively. In each quadrant, the BH sonication consisted of 25 sonication points arranged with one sonication point at a center position and the remainder divided among, and evenly spaced along, two concentric rings around a center position. The inner concentric ring had eight sonication points; the outer concentric ring had 16 sonication points. The diameter of the inner ring was 4 mm; the diameter of the outer ring was 8 mm. Within each sonication, electronic steering was used to generate the 25 sonication points. The transducer was moved mechanically between each of the four sonication locations, and moved mechanically to the central position for the volumetric HIFU thermal ablation for reference sonication.

At each of the 25 sonication points of each sonication, the BH exposure parameters were configured to generate two layers of lesions along the 4 cm depth direction of the sample (i.e., along the sagittal direction of the MR scanner). The two layers were separated by 5 mm at each sonication point. The peak applied acoustic power was 250 W. The pulse duration was 10 ms with 30 pulses per sonication point.

For the reference HIFU thermal ablation at the center of each sample, sonication was delivered as a continuous wave (CW) at 60 W at 25 points around the central position. Sonication was performed by looping 50 ms-long pulses through all the points for a total of 40 s. A single layer of lesion formation was generated by raising tissue temperature to T>60 C.

Figure 8:
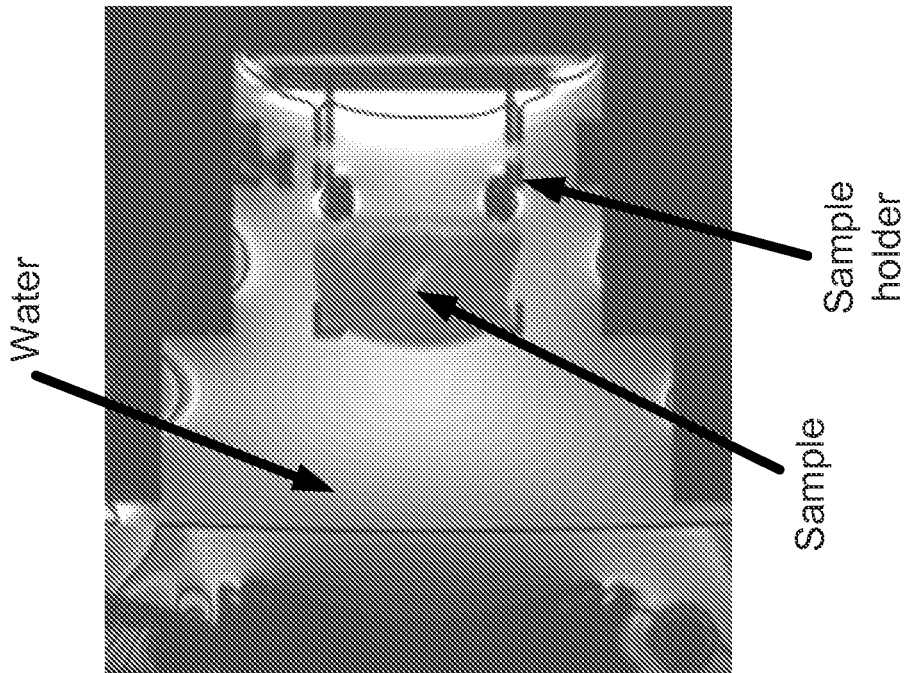
FIG. 8 depicts MRI-based planning of ultrasonic mechanical fractionation of a volume within an example object, in accordance with example embodiments.
Figure 8:
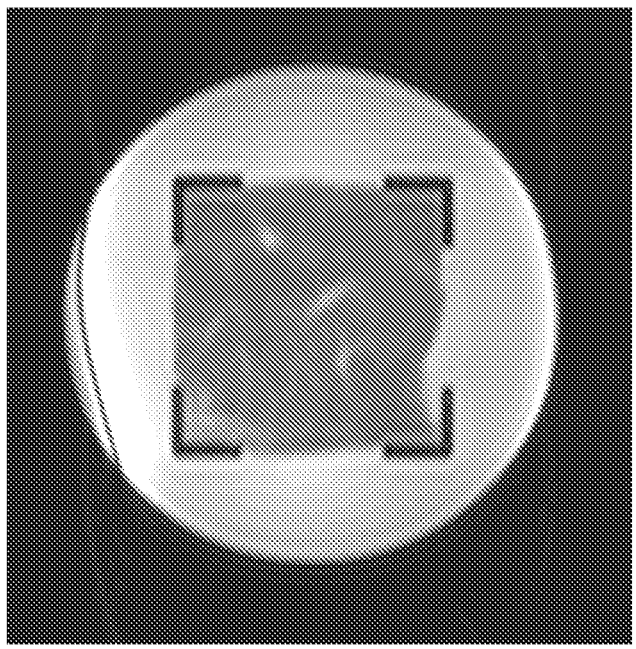

MR data were acquired prior to each sample run in order to facilitate treatment planning By way of example, treatment planning included identification of the sample geometry, visualization of blood vessels, and identification of air bubbles in the sample. FIG. 8 displays example T2-weighted images generated for treatment planning purposes.

Figure 9A:
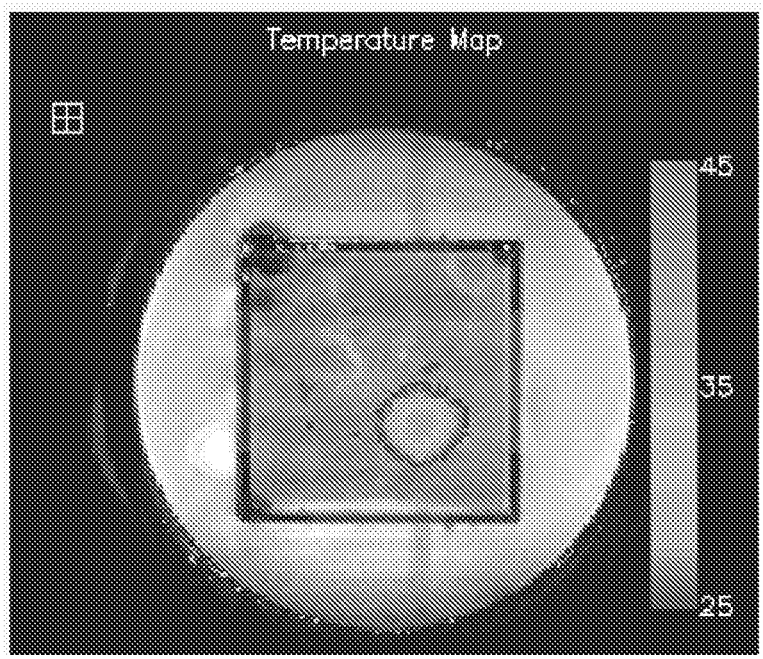
FIG. 9A shows a coronal-plane view of real-time MR temperature mapping of ultrasonic mechanical fractionation of a volume within an ex vivo bovine liver, in accordance with example embodiments.
Figure 9B:
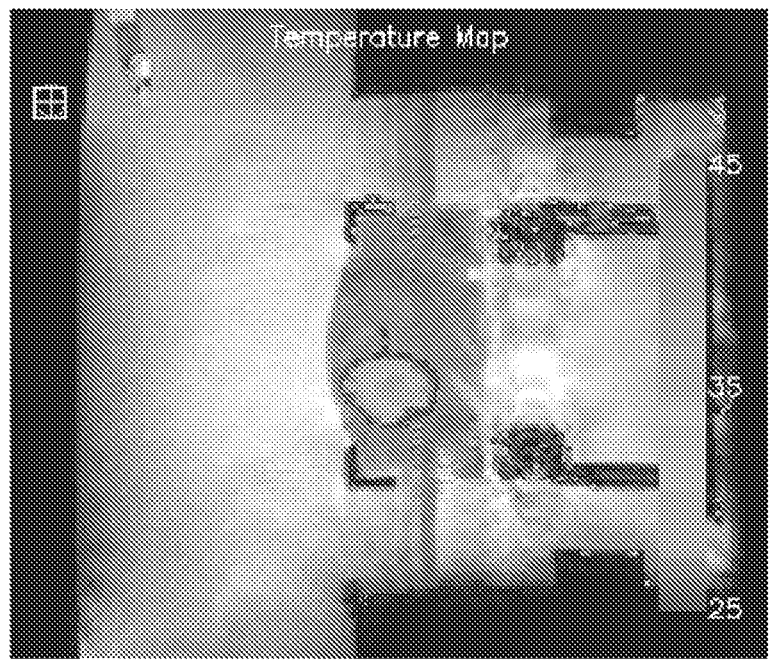

Examples of real-time monitoring of BH are shown in coronal and sagittal views in FIGS. 9A and 9B, respectively. The monitoring scheme includes a 2D multi-slice (MS) fast-field-echo (FFE) with echo-planar-imaging (EPI) MRI sequence. Six slices were acquired in two stacks (sagittal+coronal). MR parameters were TE=16 ms, TR=39 ms, and FA=19°. The voxel size was 1×1×5 mm, and the dynamic scan time was 7.5 s. Temperature maps were calculated from MR phase images using proton resonance frequency shift (PRFS) method. The maps were corrected for magnetic field drift and overlaid on MR magnitude images, as shown.

Figure 10A:
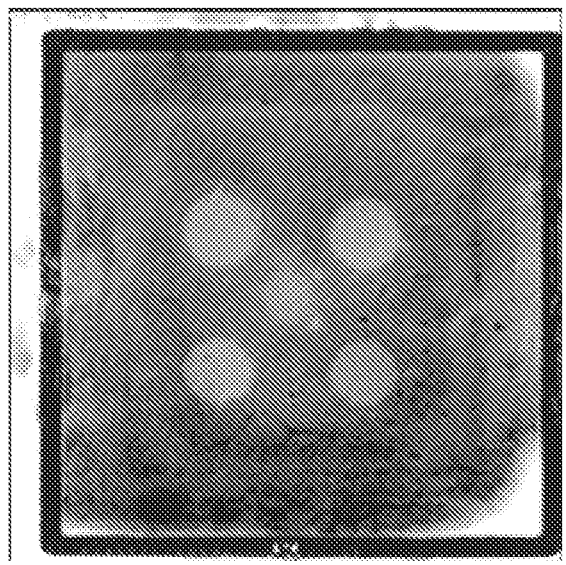
FIG. 10A shows an MR T2-weighted image of ultrasonic mechanical fractionation of a volume within an ex vivo bovine liver following sonication, in accordance with example embodiments.
Figure 10B:
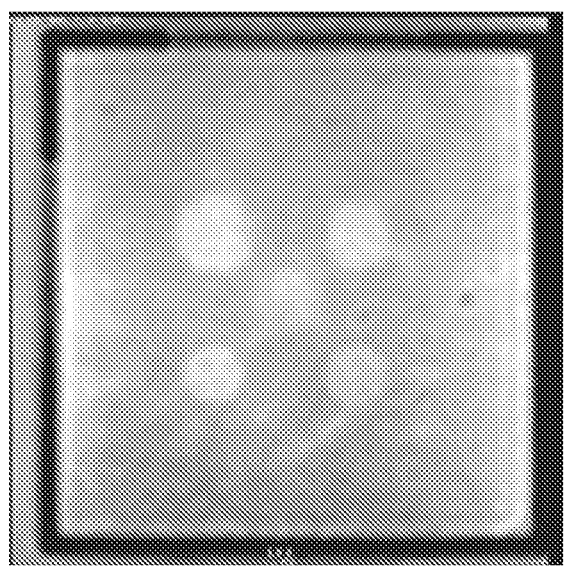
FIG. 10B shows an MR T1-weighted image of ultrasonic mechanical fractionation of a volume within an ex vivo bovine liver following sonication, in accordance with example embodiments.
Figure 10C:
FIG. 10C shows an MR T2 map of ultrasonic mechanical fractionation of a volume within an ex vivo bovine liver following sonication, in accordance with example embodiments.
Figure 10D:
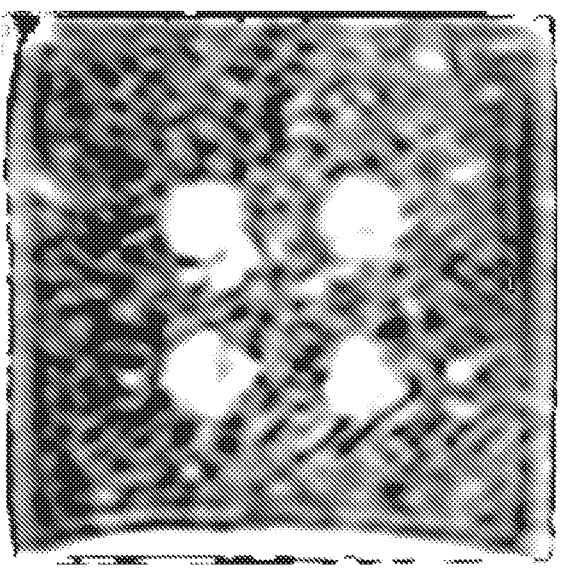
FIG. 10D shows an apparent diffusion coefficient (ADC) map of ultrasonic mechanical fractionation of a volume within an ex vivo bovine liver following sonication, in accordance with example embodiments.

Examples of post-treatment MRI are shown in FIGS. 10A-10D. Specifically, FIG. 10A shows a T2-weighted image, acquired with parameters TE=8 ms, TR=14 ms and FA=45°. FIG. 10B shows a T1-weighted image, acquired with parameters TE=23 ms, TR=633 ms and FA=90°. FIG. 10C shows a T2 map, acquired using a multi-echo Turbo-Spin Echo (TSE) sequence. FIG. 10D shows an apparent diffusion coefficient (ADC) map calculated from 2-dimensional MS DW-images, where the MR data were acquired with parameters TE=55 ms and b-value=0 and 650 s/mm$^2$.

Figures 11A, 11B:
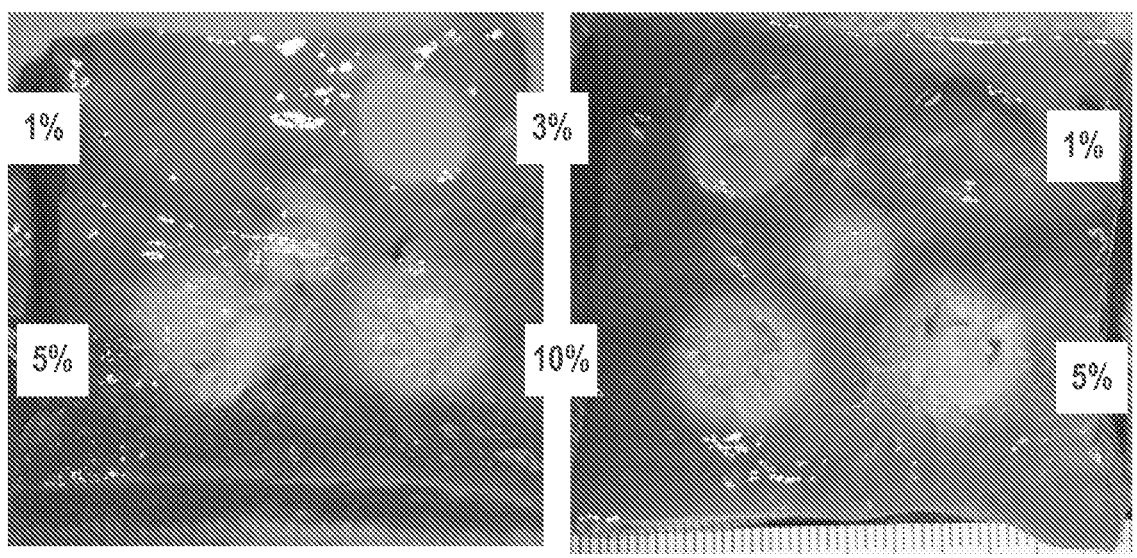
FIG. 11A shows a bottom view of lesions with content in an ex vivo bovine liver following sonication in a system configured for ultrasonic mechanical fractionation, in accordance with example embodiments.
FIG. 11B shows a top view of lesions with content in an ex vivo bovine liver following sonication in a system configured for ultrasonic mechanical fractionation, in accordance with example embodiments.
Figures 11C, 11D:
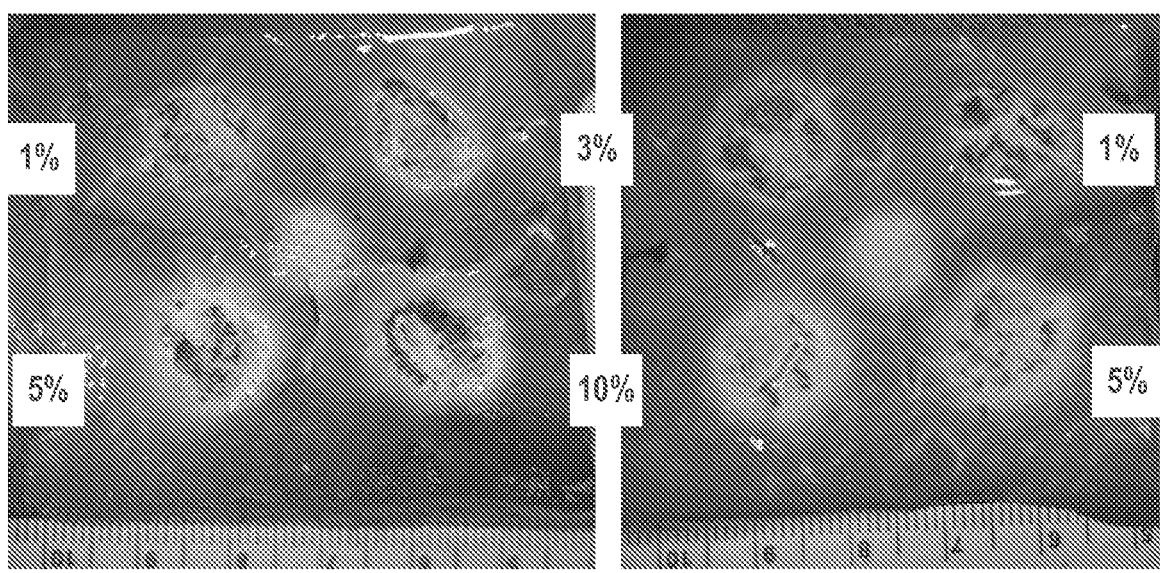
FIG. 11C shows a bottom view of water-flushed lesions in an ex vivo bovine liver following sonication in a system configured for ultrasonic mechanical fractionation, in accordance with example embodiments.
FIG. 11D shows a top view of water-flushed lesions in an ex vivo bovine liver following sonication in a system configured for ultrasonic mechanical fractionation, in accordance with example embodiments.

Examples of gross analysis of lesions produced with different duty factors are shown in FIG. 11A-11D. The four duty factors are 1%, 3%, 5% and 10%. Each figure shows an example cross section of a sonicated ex vivo bovine liver. Each of the four quadrants in each figure displays a lesion produced with BH using a different one of the duty factors, as labeled. The center of each figure shows a lesion produced by HIFU thermal ablation, as noted above. FIGS. 11A and 11B show, respectively, bottom and top views of lesions with content; FIGS. 11C and 11D show, respectively, bottom and top views of lesions flushed with water. As noted above, the peak applied acoustic power was 250 W, and the pulse duration was 10 ms with 30 pulses per sonication point.

Examples of real-time monitoring of BH shown in FIGS. 12A-12F demonstrate that lesion formation can be observed in real-time. FIGS. 12A and 12B show, respectively, coronal and sagittal view of a temperature map overlaid on MR FFE images; FIG. 12C shows temperature as a function of time over the sonication. FIGS. 12D and 12E show, respectively, coronal and sagittal view of just the underlying MR magnitude images. FIG. 12F shows a post-sonication MR magnitude FFE image of the four sonications, each having used a different one of four duty factors (1%, 3%, 5%, and 10%), as shown.

For comparison, examples of real-time monitoring of a lesion produced by conventional HIFU thermal ablation are shown in FIGS. 13A-13C. FIGS. 13A and 13B show, respectively, coronal and sagittal view of a temperature map overlaid on MR FFE images; FIG. 13C shows temperature as a function of time over the sonication. FIG. 13D shows that the lesion produced by thermal ablation is not visible in during sonication in an MR magnitude FFE image. Boiling histotripsy lesions are still visible.

Figure 14E:
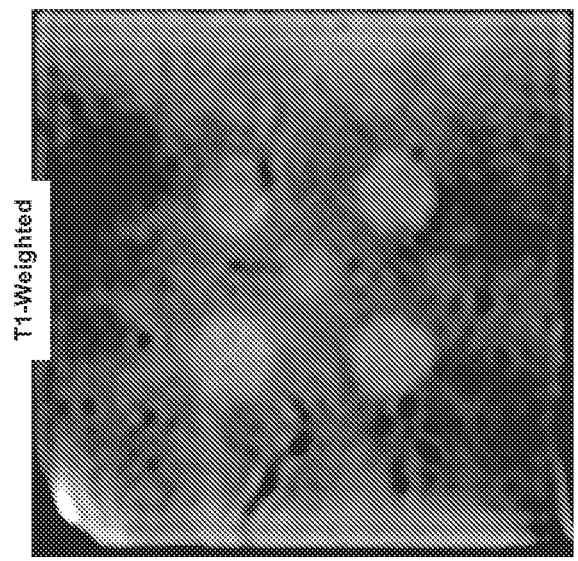
FIG. 14E is a photograph of lesions produced by ultrasonic mechanical fractionation within ex vivo bovine liver following sonication using four different duty factors, in accordance with example embodiments.
Figure 14E:
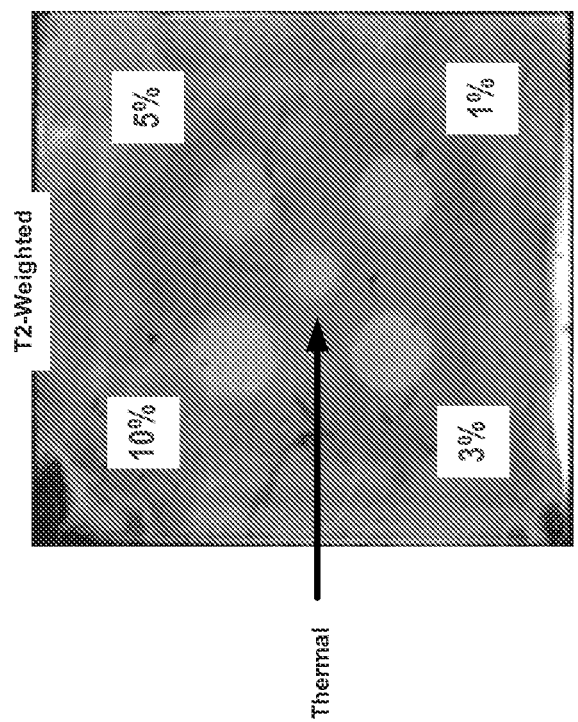
Figure 14E:
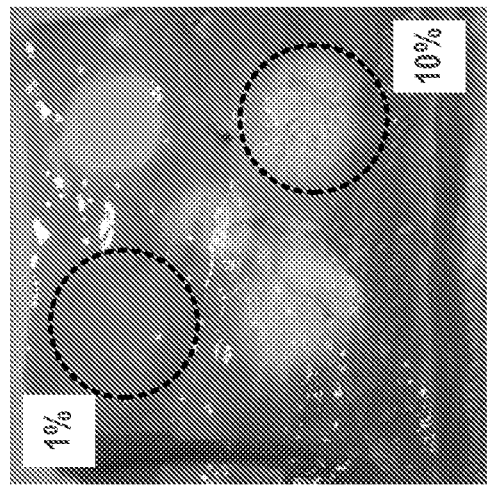
Figure 14D:
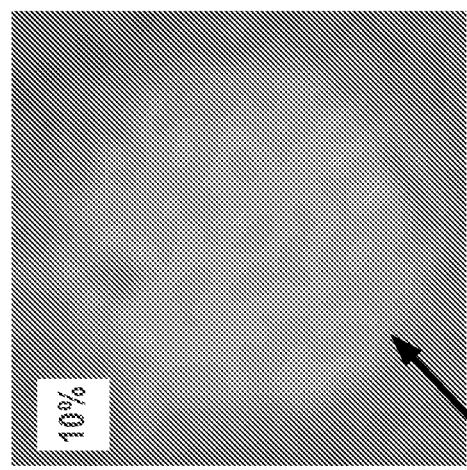
FIG. 14D shows an MR T2-weighted image of a lesion produced by ultrasonic mechanical fractionation within ex vivo bovine liver following sonication using a duty factor of 10%, in accordance with example embodiments.
Figure 14C:
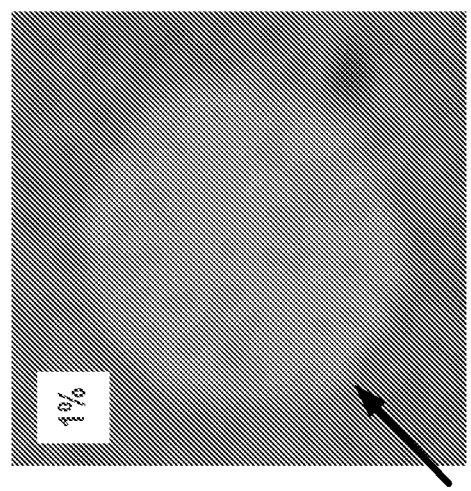
FIG. 14C shows an MR T2-weighted image of a lesion produced by ultrasonic mechanical fractionation within ex vivo bovine liver following sonication using a duty factor of 1%, in accordance with example embodiments.

FIGS. 14A-14E show various post-treatment images of lesions formed by BH, and illustrate the effect of different duty factors (duty cycles) on lesion formation. FIG. 14A shows an MR T2-weighted image of BH-induced fractionation within an ex vivo bovine liver following sonications using four different duty factors. FIG. 14B shows an MR T1-weighted image of BH-induced fractionation within an ex vivo bovine liver following sonications using the four different duty factors. FIG. 14C shows a T2-weighted MR image of a lesion produced by BH following sonication using a duty factor of 1%. FIG. 14D shows a T2-weighted MR image of a lesion produced by BH following sonication using a duty factor of 10%. FIG. 14E is a photograph of lesions produced by BH in the ex vivo bovine liver following sonication using the four different duty factors as well as the thermal ablation in the middle. Comparison of FIGS. 14C and 14D show a more sharply-defined boundary of the lesion formed using a duty factor of 1% than that formed using a duty factor or 10%. Note that as the duty cycle increases, thermal effects also increase and the mechanically ablated volume is also more thermally coagulated.

Figure 15:
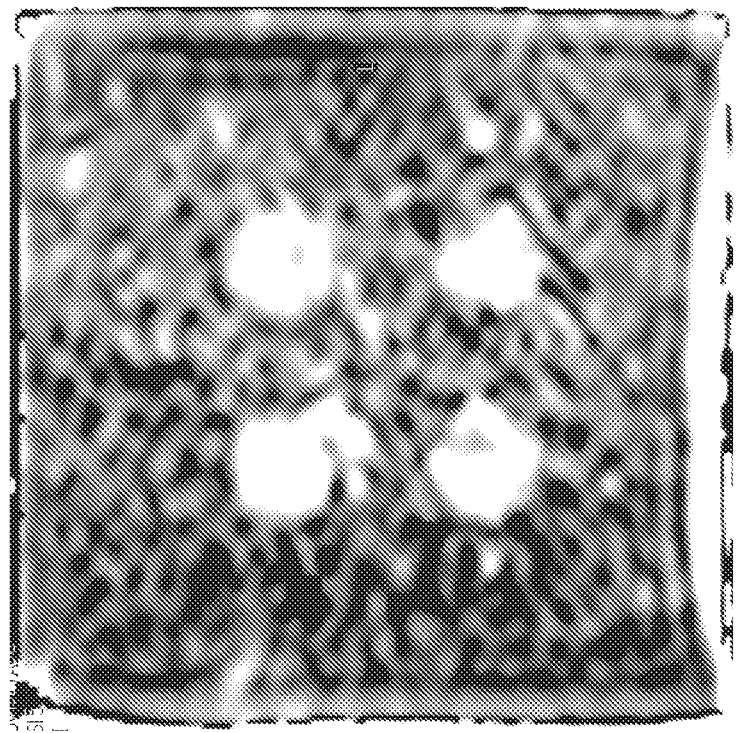
FIG. 15 shows an MR T2 map and an MR ADC map of ultrasonic mechanical fractionation of a volume within an ex vivo bovine liver following pulsed sonications using four different duty factors as well as continuous thermal sonication, in accordance with example embodiments.
Figure 15:
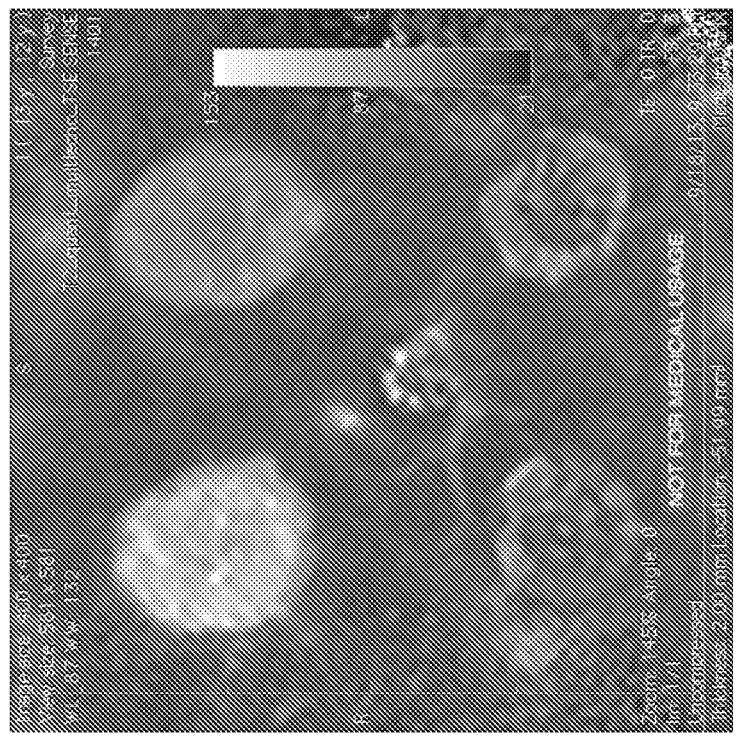

FIG. 15 shows an MR T2 map and an MR ADC map of BH-induced mechanical fractionation of a volume within an ex vivo bovine liver following sonications using four different duty factors as well as the thermal ablation in the center not visible in the ADC maps. The left side of the FIG. 15 shows a T2 map; the right side shows an ADC map. The T2 map was produced using data from the multi-echo T2-weighted TSE sequence. The two-point ADC map was produced using diffusion-weighted imaging with b-value=0 and 650 s/mm$^2$.

Figure 16:
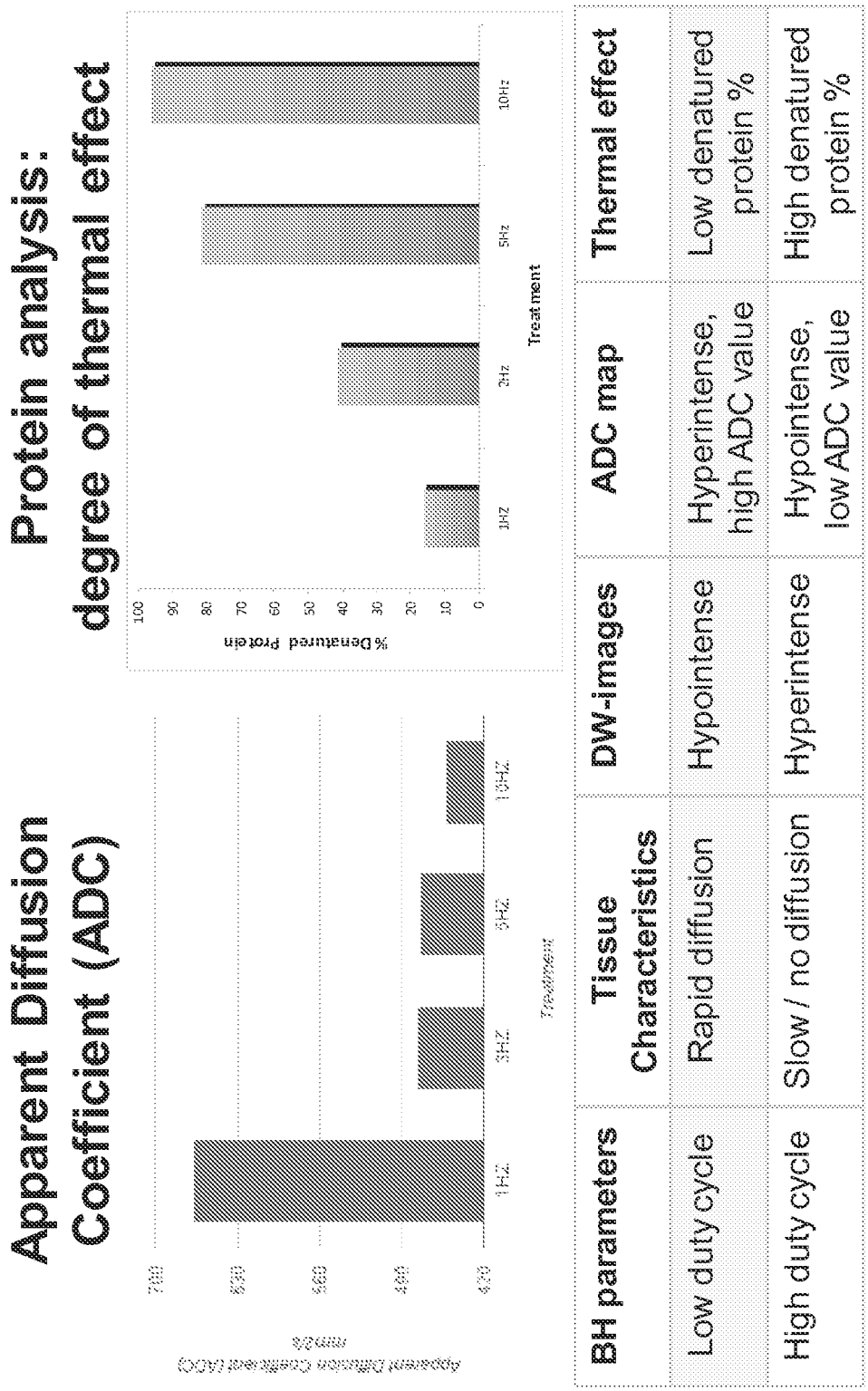
FIG. 16 shows a graphical and tabular summary of quantitative results of ultrasonic mechanical fractionation of a volume within an example object following sonications, in accordance with example embodiments.

Example results quantifying the thermal effect in mechanical lesions produced with BH and analyzed using ADC are shown graphically and in a tabular form in FIG. 16. Specifically, the upper left graph shows the ADC for each of the four duty factors. The top right graph displays a protein analysis for each of the four duty factors. The table at the bottom of the figure gives a qualitative summary of BH parameters, tissue characteristics, DW images, ADC map, and thermal effect for each of low and high duty cycles.

Results of the demonstration runs show that MRI can be used to monitor BH in real time. In addition, temperature elevation of tissue using BH is much lower than that of pure thermal ablation. This is because the rapidly heated volume is smaller than in conventional HIFU, and low duty cycle prevents strong heat accumulation. BH lesions are visible in post-therapy on T1-weighted images, T2-weighted images, and in DW MRI. Further, fractioned and thermal lesions can be differentiated. Finally, the degree of thermal effect in mechanically ablated lesions can be quantified using ADC and T2 maps.

5. Example Methods

Figure 17:
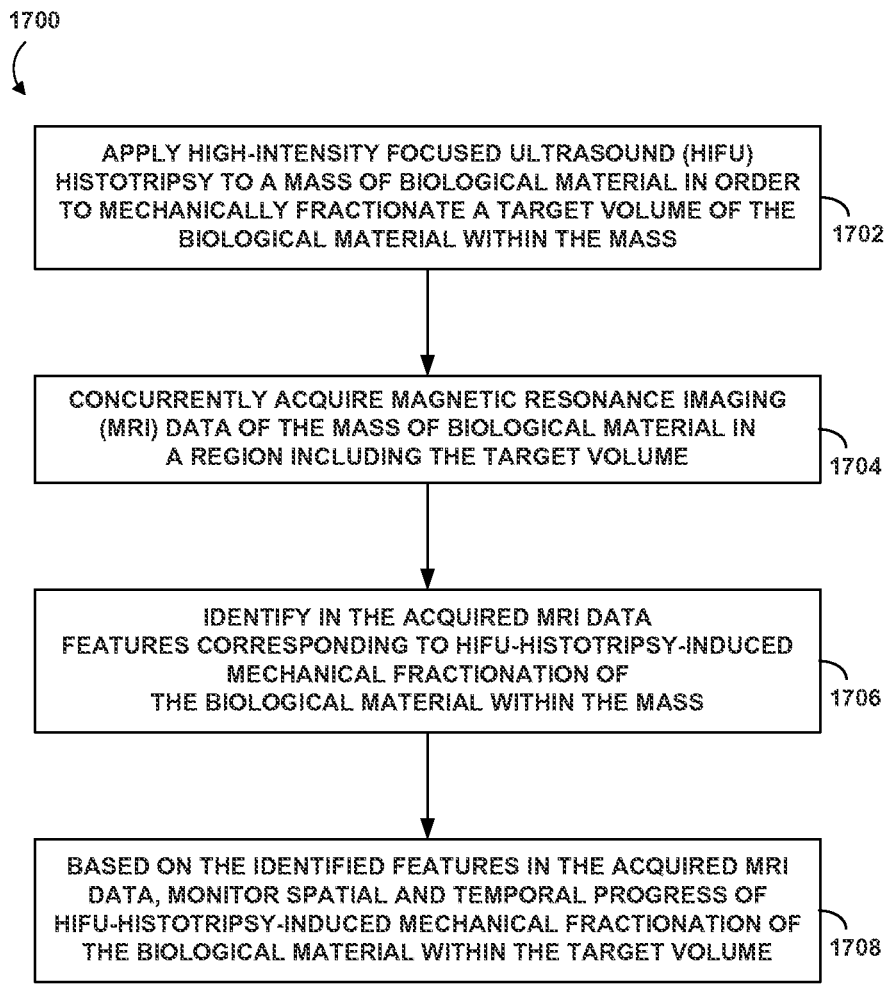
FIG. 17 is a flow chart depicting one example method for MR monitoring of ultrasonic mechanical fractionation of a volume within an object during sonication, in accordance with example embodiments.
Figure 18:
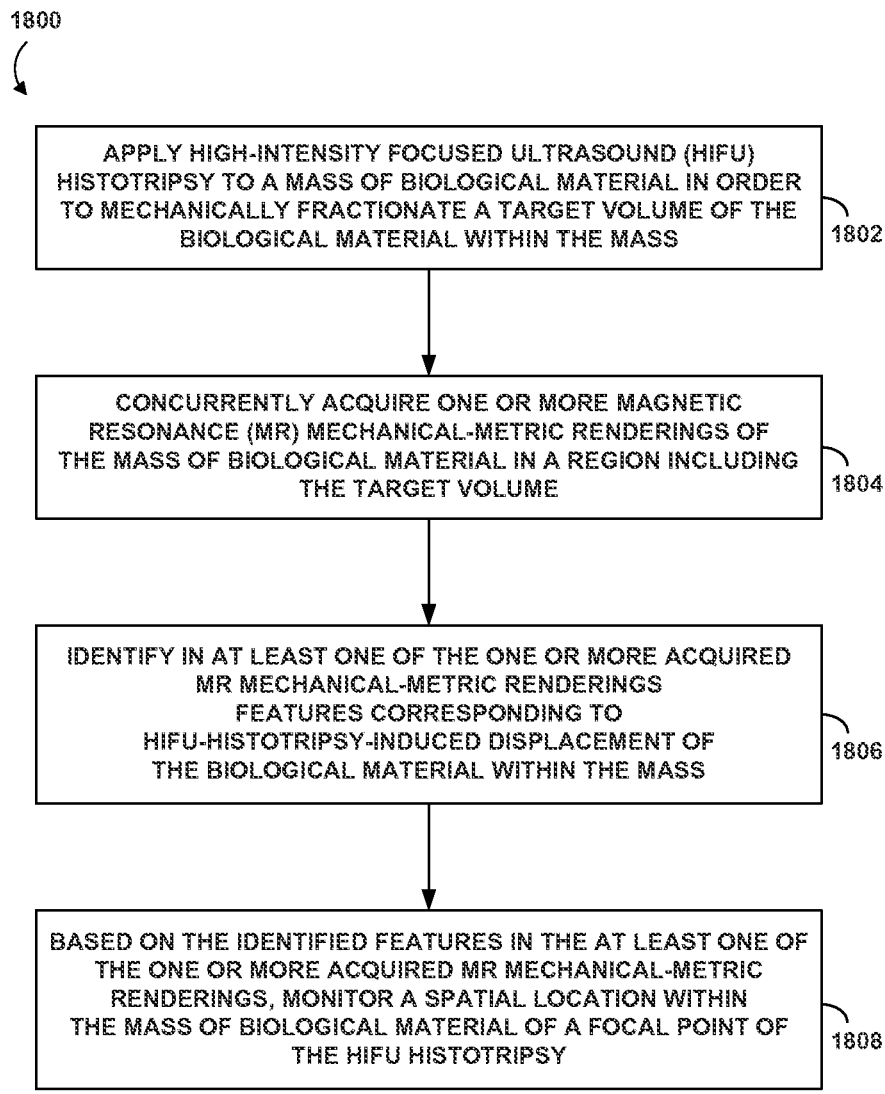
FIG. 18 is a flow chart depicting another example method for MR monitoring of ultrasonic mechanical fractionation of a volume within an object during sonication, in accordance with example embodiments.
Figure 19:
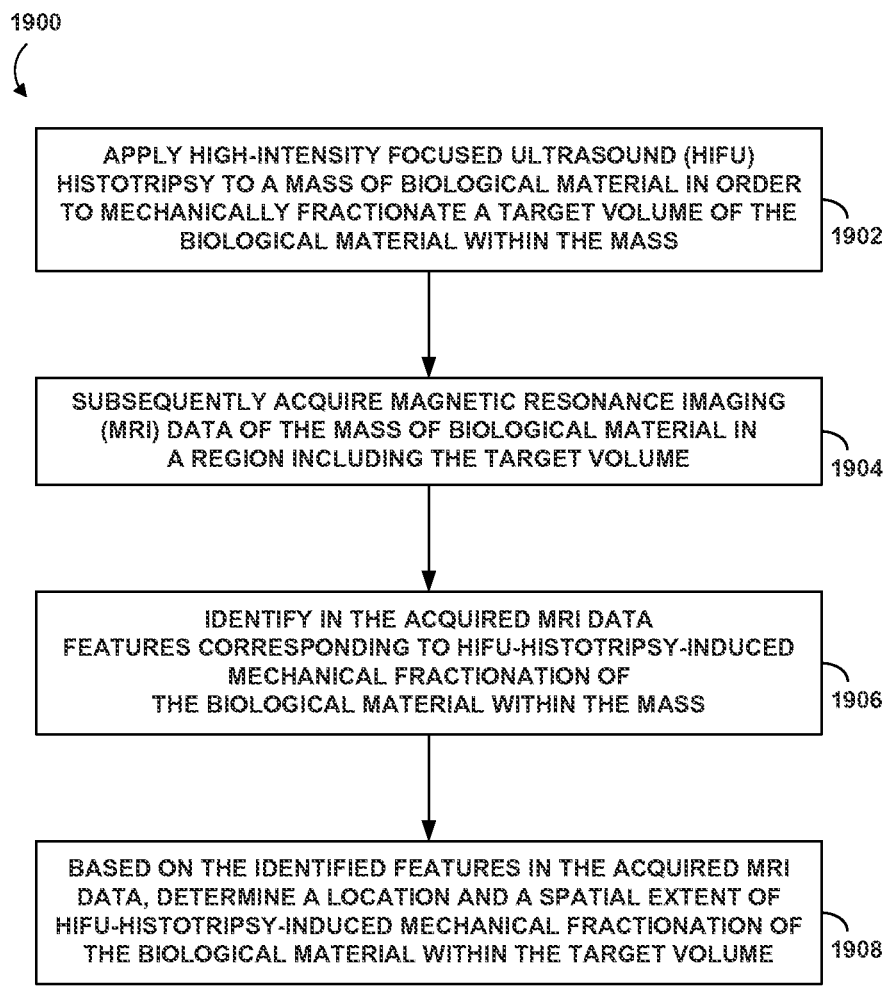
FIG. 19 is a flow chart depicting an example method for MR evaluation of ultrasonic mechanical fractionation of a volume within an object following sonication, in accordance with example embodiments.

FIGS. 17, 18, and 19 are flow charts illustrating example methods 1700, 1800, and 1900, respectively, according to example embodiments. Illustrative methods, such as methods 1700, 1800, and 1900, may be carried out in whole or in part by a system such as the one described above. More specifically, the methods 1700, 1800, and 1900 can be carried out by system that includes a high-intensity focused ultrasound (HIFU) histotripsy subsystem, a magnetic resonance imaging (MRI) subsystem, one or more processors, and memory accessible to the one or more processors. The demonstration system described above is an example of system in which the methods 1700, 1800, and 1900 can be carried out.

By way of example, the methods 1700, 1800, and 1900 can be implemented as machine language instructions that can be stored on non-transient machine-readable media (e.g, solid state memory, magnetic disk, etc), such as the memory of the system, and that when executed by one or more processors of a system to cause the system to carry out operations, steps, and/or functions of the method. Each of methods 1700, 1800, and 1900 are discussed below in turn.

Considering first method 1700 in FIG. 17, block 1702 shows that method 1700 involves applying high-intensity focused ultrasound (HIFU) histotripsy to a mass of biological material in order to mechanically fractionate a target volume of the biological material within the mass.

As shown by block 1704 in FIG. 17, method 1700 also involves concurrently with applying the HIFU histotripsy to the mass of biological material, acquiring magnetic resonance imaging (MRI) data of the mass of biological material in a region including the target volume.

As shown by block 1706 in FIG. 17, method 1700 further involves identifying in the acquired MRI data features corresponding to HIFU-histotripsy-induced mechanical fractionation of the biological material within the mass.

Finally, as shown by block 1708 in FIG. 17 method 1700 then involves, based on the identified features in the acquired MRI data, monitoring spatial and temporal progress of HIFU-histotripsy-induced mechanical fractionation of the biological material within the target volume.

In accordance with example embodiments, the HIFU histotripsy applied to the biological material can be boiling histotripsy (BH). As such, the BH can be applied by adapting parameters of HIFU sonication, as described above. Such parameters include HIFU pulse duration, HIFU pulse shock amplitude, HIFU power, HIFU pulse duty cycle, and number of pulses.

Also in accordance with example embodiments, acquiring the MRI data can entail acquiring one or more MRI renderings of the mass of biological material in a region including the target volume. As discussed above, MRI renderings can correspond to various forms in which MR data can be represented and/or presented. Non-limiting examples of MRI renderings include diffusion-weighted images, T1-weighted images, T2-weighted images, proton density-weighted images, T1 maps, T2 maps, T1*-weighted images, T2*-weighted images, T2* maps, T1-ρ-weighted images, fluid attenuated inversion recovery (FLAIR) images, susceptibility-weighted images (SWIs), diffusion maps, or a combined MRI rendering of at least two of the preceding renderings.

Identifying features corresponding to HIFU-histotripsy-induced mechanical fractionation of the material within the mass in the acquired MRI data can entail identifying contrasting features corresponding to a portion of mechanically fractionated biological material within the mass in at least one of the one or more acquired MRI renderings. In particular, the contrasting features can be identified during real-time monitoring of HIFU histotripsy sonication. By way of example, a time sequence of multiple MRI renderings can be acquired during a time interval that is concurrent with applying the HIFU histotripsy to the mass of biological material. Then, real-time monitoring can entail comparing contrasting features that appear in one or more of the time sequence of the multiple MRI renderings. That is, by comparing each MRI rendering at a given time in the time sequence MRI renderings at earlier times in the time sequence, an evolution of contrasting features across the time sequence can be used to determine or infer spatial evolution of HIFU-histotripsy-induced mechanical fractionation of the biological material within the target volume over the time interval.

Identifying contrasting features corresponding to a portion of mechanically fractionated biological material within the mass in at least one of the one or more acquired MRI renderings can also serve the monitoring process by helping to identify a boundary between mechanically fractionated biological material and intact biological material. More specifically, a first contrasting feature may be identified as mechanically fractionated biological material within the mass, while a second contrasting feature may be identified as intact biological material within the mass. A boundary between the first and second contrasting features can then be identified as a physical boundary between the mechanically fractionated biological material and the intact biological material.

In some applications, the biological material can be infused with a contrast agent prior to or during acquiring the MRI data. Doing so can help increase the apparent contrast seen in one or more of the MRI renderings.

In further accordance with example embodiments, the method 1700 can also include controlling subsequent application of the HIFU histotripsy to the mass of biological material. More specifically, controlling subsequent application of the HIFU histotripsy to the mass of biological material can entail providing feedback control to application of the HIFU histotripsy to the mass of biological material. In one example, the feedback control can be part of an automatic control process. In another example, the feedback control can be part of manual control process applied by an operator of the system. In still another example, feedback control may involve a mix of both automatic and manual control.

Controlling subsequent application of the HIFU histotripsy to the mass of biological material can also entail adjusting application of the HIFU histotripsy based on features identified in one or more MRI renderings acquired during sonication. For example, a first contrasting feature might be identified as mechanically fractionated biological material within the target volume, and a second feature might be identified as intact biological material within the target volume. Application of the HIFU histotripsy can then be adjusted so as to cause mechanical fractionation of the intact biological material within the target volume. By way of example, adjusting HIFU histotripsy can entail adjusting a spatial location of a focal point of the HIFU histotripsy, adjusting a duration of the HIFU histotripsy, adjusting HIFU pulse parameters, adjusting HIFU pulse power, adjusting HIFU pulse duty cycle, or some mix of these adjustments.

Other forms of MRI data can be acquired as well. In one example, acquiring the MRI data of the mass of biological material in the region including the target volume can entail acquiring one or more MRI thermal-metric maps of the mass of biological material in a region including the target volume. Non-limiting examples of MRI thermal-metric maps include MRI temperature maps and MRI thermal dose maps. In accordance with example embodiments, identifying features corresponding to HIFU-histotripsy-induced mechanical fractionation of biological material within the mass can then entail identifying within the one or more acquired MRI thermal-metric maps a gradient indicative of a physical boundary between the target volume and a region exterior to the target volume. The gradient could be a temperature gradient or a thermal-dose gradient.

As with MRI renderings, multiple thermal-metric maps can be acquired in a time sequence during a time interval that is concurrent with applying the HIFU histotripsy to the mass of biological material. Then, real-time monitoring can entail determining a thermal-property distribution within the target volume for each of the multiple MRI thermal-metric maps of the time sequence. By comparing the thermal-property distribution in an MRI thermal-metric map at each time with similar distributions in thermal-metric maps earlier in the time sequence, spatial and temporal evolution of HIFU-histotripsy-induced liquefaction within the target volume can be determined or inferred. Non-limiting examples of a thermal-property distribution include temperature distributions, temperature gradients, thermal-dose distributions, and thermal-dose gradients.

In further accordance with example embodiments, MRI-assisted HIFU histotripsy (e.g., BH) using thermal-metric maps can entail controlling subsequent application of the HIFU histotripsy to the mass of biological material. The description of feedback-based control of HIFU histotripsy in the context of MRI renderings applies to control in the context of thermal-metric maps as well.

Controlling subsequent application of the HIFU histotripsy using thermal-metric maps can also entail determining whether to continue or cease sonication. More particularly, thermal-metric maps can be used to determine a temperature property within the target volume. If the determined temperature property is no greater than a corresponding threshold temperature property, then application of the HIFU histotripsy within the target volume can be continued. If the determined temperature property is greater than the corresponding threshold temperature property, then application of the HIFU histotripsy within the target volume would be paused or discontinued. Non-limiting examples of the temperature property include a maximum temperature, a mean temperature, and a median temperature.

As discussed above, the biological material can be biological tissue or a biological substance. Non-limiting examples of biological tissue include liver tissue, uterine tissue, kidney tissue, prostate tissue, thyroid tissue, pancreas tissue, brain tissue, nerve tissue, connective tissue, or muscle tissue. Non-limiting examples of a biological substance include a blood clot or a hematoma. Non-limiting examples of therapeutic application of MRI-assisted HIFU histotripsy (e.g., BH) include treatment of pathological tissue, such as malignant tumors (e.g., gliomas, melanomas, or carcinomas) and benign tumors (e.g., adenomas or fibroids).

Considering next method 1800 in FIG. 18, block 1802 shows that method 1800 involves applying high-intensity focused ultrasound (HIFU) histotripsy to a mass of biological material in order to mechanically fractionate a target volume of biological material within the mass.

As shown by block 1804 in FIG. 1800, method 1800 also involves concurrently with applying the HIFU histotripsy to the mass of biological material, acquiring one or more magnetic resonance (MR) mechanical-metric renderings of the mass of biological material in a region including the target volume. Non-limiting examples of MR mechanical-metric renderings include magnetic resonance elastography (MRE) images, magnetic resonance acoustic radiation force images (MR-ARFIs), elasticity maps, and displacement maps.

As shown by block 1806 in FIG. 1800, method 1800 further involves identifying in at least one of the one or more acquired MR mechanical-metric renderings features corresponding to HIFU-histotripsy-induced displacement or elasticity/stiffness of the biological material within the mass.

Finally, as shown by block 1808 in FIG. 18 method 1800 then involves, based on the identified features in the at least one of the one or more acquired MR mechanical-metric renderings, monitoring a spatial location within the mass of biological material of a focal point of the HIFU histotripsy.

In accordance with example embodiments, the HIFU histotripsy applied to the biological material can be boiling histotripsy (BH). As such, the BH can be applied by adapting parameters of HIFU sonication, as described above. Such parameters include HIFU pulse parameters, HIFU pulse length, power, and HIFU pulse duty cycle.

In further accordance with example embodiments, the method 1800 can also include adjusting application of the HIFU histotripsy within the mass of biological material based on the one or more acquired MR mechanical-metric renderings. More particularly, adjusting application of the HIFU histotripsy can entail adjusting a spatial location of a focal point of the HIFU histotripsy or adjusting a duration of the HIFU histotripsy. Further, adjusting application of the HIFU histotripsy can entail can entail providing feedback control to application of the HIFU histotripsy to the mass of biological material. In one example, the feedback control can be part of an automatic control process. In another example, the feedback control can be part of manual control process applied by an operator of the system. In still another example, feedback control may involve a mix of both automatic and manual control.

As with the method 1700, the biological material in the method 1800 can be biological tissue or a biological substance. Again, non-limiting examples of biological tissue include liver tissue, uterine tissue, kidney tissue, prostate tissue, thyroid tissue, pancreas tissue, brain tissue, nerve tissue, connective tissue, or muscle tissue. Non-limiting examples of a biological substance include a blood clot or a hematoma. Non-limiting examples of therapeutic application of MRI-assisted HIFU histotripsy (e.g., BH) include treatment of pathological tissue, such as malignant tumors (e.g., gliomas, melanomas, or carcinomas) and benign tumors (e.g., adenomas or fibroids).

Considering finally method 1900 in FIG. 19, block 1902 shows that method 1900 involves applying high-intensity focused ultrasound (HIFU) histotripsy to a mass of biological material in order to mechanically fractionate a target volume of the biological material within the mass.

As shown by block 1904 in FIG. 19, method 1900 also involves subsequent to applying the HIFU histotripsy to the mass of biological material, acquiring magnetic resonance imaging (MRI) data of the mass of biological material in a region including the target volume.

As shown by block 1906 in FIG. 19, method 1900 further involves identifying in the acquired MRI data features corresponding to HIFU-histotripsy-induced mechanical fractionation of the biological material within the mass.

Finally, as shown by block 1908 in FIG. 19 method 1900 then involves, based on the identified features in the acquired MRI data, determining a location and a spatial extent of HIFU-histotripsy-induced mechanical fractionation of the biological material within the target volume.

In accordance with example embodiments, the HIFU histotripsy applied to the biological material can be boiling histotripsy (BH). As such, the BH can be applied by adapting parameters of HIFU sonication, as described above. Such parameters include HIFU pulse parameters, HIFU pulse length, power, and HIFU pulse duty cycle.

Also in accordance with example embodiments, acquiring the MRI data can entail acquiring one or more MRI renderings of the mass of biological material in a region including the target volume. As discussed above, MRI renderings can correspond to various forms in which MR data can be represented and/or presented. Non-limiting examples of MRI renderings include diffusion-weighted images, T1-weighted images, T2-weighted images, proton density-weighted images, T1 maps, T2 maps, T1*-weighted images, T2*-weighted images, T2* maps, T1-ρ-weighted images, fluid attenuated inversion recovery (FLAIR) images, susceptibility-weighted images (SWIs), diffusion maps, or a combined MRI rendering of at least two of the preceding renderings.

Identifying features corresponding to HIFU-histotripsy-induced mechanical fractionation of the material within the mass in the acquired MRI data can entail identifying contrasting features corresponding to a portion of mechanically fractionated biological material within the mass in at least one of the one or more acquired MRI renderings. In particular, identifying contrasting features can help determine a spatial extent of HIFU-histotripsy-induced mechanical fractionation of the biological material within the target volume. Specifically, a first contrasting feature may be identified as mechanically fractionated biological material within the mass, while a second contrasting feature may be identified as intact biological material within the mass. A boundary between the first and second contrasting features can then be identified as a physical boundary between the mechanically fractionated biological material and the intact biological material.

In some applications, the biological material can be infused with a contrast agent prior to or during acquiring the MRI data. Doing so can help increase the apparent contrast seen in one or more of the MRI renderings.

As with the methods 1700 and 1800, the biological material in the method 1900 can be biological tissue or a biological substance. Again, non-limiting examples of biological tissue include liver tissue, uterine tissue, kidney tissue, prostate tissue, thyroid tissue, pancreas tissue, brain tissue, nerve tissue, connective tissue, or muscle tissue. Non-limiting examples of a biological substance include a blood clot or a hematoma. Non-limiting examples of therapeutic application of MRI-assisted HIFU histotripsy (e.g., BH) include treatment of pathological tissue, such as malignant tumors (e.g., gliomas, melanomas, or carcinomas) and benign tumors (e.g., adenomas or fibroids).

In further accordance with example embodiments, the method 1900 can also include determining whether or not to resume application of the HIFU histotripsy to the mass of biological material an outcome of post-sonication evaluation of results indicate from the MRI data acquired subsequent to application of the HIFU-based histotripsy. For example, a determination to resume sonication could be based on the determined location and spatial extent of HIFU-histotripsy-induced mechanical fractionation of the biological material within the target volume. It could also be based further on a degree of mechanical fractionation of the biological material within the target volume. Further, a determination to resume sonication could be based on both extent and degree of HIFU-histotripsy-induced mechanical fractionation of the biological material within the target volume.

It will be appreciated that the steps of the methods 1700, 1800, and 1900 are presented by way of example, and that for any of the methods 1700, 1800, and 1900, additional and/or alternative steps or alternative ordering of steps could be carried out and still remain within the scope and spirit of the embodiments herein.

CONCLUSION

An illustrative embodiment has been described by way of example herein. Those skilled in the art will understand, however, that changes and modifications may be made to this embodiment without departing from the true scope and spirit of the elements, products, and methods to which the embodiment is directed, which is defined by the claims.

REFERENCES

1. Kim Y S, Keserci B, Partanen A, Rhim H, Lim H K, Park M J, Köhler MO. Volumetric MRI-HIFU ablation of uterine fibroids: role of treatment cell size in the improvement of energy efficiency. Eur J Radiol. 2012 Nov.; 81(11):3652-9.
2. M. Canney, V. Khokhlova, O. Bessonova, M. Bailey, L. Crum. Shock-induced heating and millisecond boiling in gels and tissue due to high intensity focused ultrasound, Ultrasound in Medicine & Biology, 2010, v.36(2), pp. 250-267.
3. T. D. Khokhlova, M. S. Canney, V. A. Khokhlova, O. A. Sapozhnikov, L. A. Crum, M. R. Bailey. Controlled tissue emulsification produced by high intensity focused ultrasound shock waves and millisecond boiling. J. Acoust. Soc. Am., 2011, v.130(5), pp. 3498-3510.
4. Y.-N. Wang, T. D. Khokhlova, M. R. Bailey, J.-H. Hwang, V. A. Khokhlova. Histological and biochemical analysis of mechanical and thermal bioeffects in boiling histotripsy lesions induced by high intensity focused ultrasound. Ultrasound in Medicine & Biology, 2013, v. 39(3), pp. 424-438.
5. J. C. Simon, O. A. Sapozhnikov, V. A. Khokhlova, Y.-N. Wang, L. A. Crum, and M. R. Bailey. Ultrasonic atomization of tissue and its role in tissue fractionation by high intensity focused ultrasound. Phys. Med. Biol., 2012, v. 57(2)3, pp. 8061-8078.
6. Maxwell, O. Sapozhnikov, M. Bailey, L. Crum, Z. Xu, B. Fowlkes, C. Cain, V. Khokhlova. Disintegration of tissue using high intensity focused ultrasound: Two approaches that utilize shock waves. 2012, Acoustics Today, v. 8(4), pp. 24-36.
7. W. Kreider, P. V. Yuldashev, O. A. Sapozhnikov, N. Fan, A. Partanen, M. R. Bailey, and V. A. Khokhlova. Characterization of a multi-element clinical HIFU system using acoustic holography and nonlinear modeling. IEEE Trans. Ultrason., Ferroelect., Freq. Contr., 2013, v. 60(8), pp. 1683-1698.
8. Köhler MO, Mougenot C, Quesson B, Enholm J, Le Bail B, Laurent C, Moonen C T, Ehnholm G J. Volumetric HIFU ablation under 3D guidance of rapid MRI thermometry. Med Phys. 2009 Aug.; 36(8):3521-35.

All of the above references are incorporated herein by reference in their entireties.

We claim:

1. A method comprising:
    applying high-intensity focused ultrasound (HIFU) histotripsy to a target volume of biological material;
    concurrently with applying the HIFU histotripsy to the target volume, acquiring magnetic resonance imaging (MRI) data from the target volume;
    identifying a first feature of the MRI data as corresponding to mechanically fractionated biological material within the target volume;
    identifying a second feature of the MRI data as corresponding to intact biological material within the target volume; and
    adjusting application of the HIFU histotripsy to cause mechanical fractionation of the intact biological material by at least one of: (i) adjusting a spatial location of a focal point of the HIFU histotripsy, (ii) adjusting a duration of the HIFU histotripsy, (iii) adjusting HIFU pulse parameters, (iv) adjusting HIFU pulse power, or (v) adjusting HIFU pulse duty cycle,
    wherein applying the HIFU histotripsy to the target volume comprises applying boiling histotripsy (BH) to the target volume,
    wherein acquiring the MRI data comprises: acquiring one or more MRI thermal-metric maps of the target volume,
    wherein each of the one or more MRI thermal-metric maps is one of an MRI temperature map or an MRI thermal dose map, and
    wherein acquiring the one or more MRI thermal-metric maps comprises:
    acquiring a time sequence of multiple MRI thermal-metric maps during a time interval that is concurrent with applying the HIFU histotripsy, the method further comprising:
    monitoring spatial and temporal progress of HIFU-histotripsy-induced mechanical fractionation of the target volume by:
    determining a thermal-property distribution within the target volume for each of the multiple MRI thermal-metric maps of the time sequence, wherein the thermal-property distribution is one of a temperature distribution, a temperature gradient, a thermal-dose distribution, or a thermal-dose gradient; and
    comparing the thermal-property distribution in an MRI thermal-metric map at each time in the time sequence of the multiple MRI thermal-metric maps with the thermal-property distributions in one or more of the multiple MRI thermal-metric maps earlier in the time sequence, and determining spatial evolution of HIFU-histotripsy-induced liquefaction of the biological material within the target volume over the time interval.

2. The method of claim 1, wherein acquiring the MRI data comprises:
    acquiring one or more MRI renderings of the target volume.

3. The method of claim 2, wherein each of the one or more MRI renderings is one of: (i) a diffusion-weighted image, (ii) a T1-weighted image, (iii) a T2-weighted image, (iv) a proton density-weighted image, (v) a T1 map, (vi) a T2 map, (vii) a T1*-weighted image, (viii) a T2*-weighted image, (ix) a T2* map, (x) a T1-p-weighted image, (xi) a fluid attenuated inversion recovery (FLAIR) image, (xii) a susceptibility-weighted image (SWI), (xiii) a diffusion map, or (xiv) a combined MRI rendering of at least two of (i)-(xiii).

4. The method of claim 2, wherein acquiring the one or more MRI renderings comprises:
    acquiring a time sequence of multiple MRI renderings during a time interval that is concurrent with applying the HIFU histotripsy to the target volume, the method further comprising:
    based on the acquired MRI data, monitoring spatial and temporal progress of HIFU-histotripsy-induced mechanical fractionation of the target volume by:
    comparing contrasting features in an MRI rendering at each time in the time sequence of the multiple MRI renderings with contrasting features in one or more of the multiple MRI renderings earlier in the time sequence, and determining spatial evolution of HIFU-histotripsy-induced mechanical fractionation of the target volume over the time interval.

5. The method of claim 2, further comprising:
    identifying a boundary between the first feature and the second feature as a physical boundary between the mechanically fractionated biological material and the intact biological material.

6. The method of claim 1, further comprising infusing the target volume with a contrast agent prior to or while acquiring the MRI data.

7. The method of claim 1, further comprising:
    based on the acquired MRI data, controlling subsequent application of the HIFU histotripsy.

8. The method of claim 7, wherein controlling subsequent application of the HIFU histotripsy comprises:
providing feedback control to application of the HIFU histotripsy according to at least one of an automatic control process or a manual control process.

9. The method of claim 1, further comprising:
identifying, within the one or more acquired MRI thermal-metric maps, a gradient indicative of a physical boundary between the target volume and a region exterior to the target volume, wherein the gradient is at least one of a temperature gradient or a thermal-dose gradient.

10. The method of claim 1, further comprising:
based on the one or more acquired MRI thermal-metric maps, controlling subsequent application of the HIFU histotripsy.

11. The method of claim 10, wherein controlling subsequent application of the HIFU histotripsy comprises:
providing feedback control to application of the HIFU histotripsy according to at least one of an automatic control process or a manual control process.

12. The method of claim 10, further comprising:
determining a temperature property within the target volume, wherein the temperature property is one of a maximum temperature, a mean temperature, or a median temperature;
when the determined temperature property is no greater than a corresponding threshold temperature property, then continuing applying the HIFU histotripsy within the target volume; and
when the determined temperature property is greater than the corresponding threshold temperature property, then doing one of pausing or discontinuing applying the HIFU histotripsy within the target volume.

13. The method of claim 1, wherein the biological material is at least one of biological tissue or a biological substance,
wherein the biological tissue is at least one of liver tissue, uterine tissue, kidney tissue, prostate tissue, thyroid tissue, pancreas tissue, brain tissue, nerve tissue, connective tissue, or muscle tissue,
and wherein the biological substance is at least a portion of one of a blood clot or a hematoma.

14. The method of claim 1, wherein the target volume at least partially overlaps with pathological tissue, the pathological tissue being one of a malignant tumor or benign tumor,
wherein the malignant tumor is one of a glioma, a melanoma, or a carcinoma,
and wherein the benign tumor is one of an adenoma or a fibroid.

15. An apparatus comprising:
a high-intensity focused ultrasound (HIFU) histotripsy subsystem;
a magnetic resonance imaging (MRI) subsystem;
one or more processors;
memory accessible to the one or more processors, and storing instructions that, upon execution by the one or more processors, cause the apparatus to carry out operations including:
applying high-intensity focused ultrasound (HIFU) histotripsy to a target volume of biological material;
concurrently with applying the HIFU histotripsy to the target volume, acquiring magnetic resonance imaging (MRI) data from the target volume;
identifying a first feature of the MRI data as corresponding to mechanically fractionated biological material within the target volume;
identifying a second feature of the MRI data as corresponding to intact biological material within the target volume; and
adjusting application of the HIFU histotripsy to cause mechanical fractionation of the intact biological material by at least one of: (i) adjusting a spatial location of a focal point of the HIFU histotripsy, (ii) adjusting a duration of the HIFU histotripsy, (iii) adjusting HIFU pulse parameters, (iv) adjusting HIFU pulse power, or (v) adjusting HIFU pulse duty cycle,
wherein applying the HIFU histotripsy to the target volume comprises applying boiling histotripsy (BH) to the target volume,
wherein acquiring the MRI data comprises: acquiring one or more MRI thermal-metric maps of the target volume, wherein each of the one or more MRI thermal-metric maps is one of an MRI temperature map or an MRI thermal dose map, and
wherein acquiring the one or more MRI thermal-metric maps comprises:
acquiring a time sequence of multiple MRI thermal-metric maps during a time interval that is concurrent with applying the HIFU histotripsy, the operations further comprising:
monitoring spatial and temporal progress of HIFU-histotripsy-induced mechanical fractionation of the target volume by:
determining a thermal-property distribution within the target volume for each of the multiple MRI thermal-metric maps of the time sequence, wherein the thermal-property distribution is one of a temperature distribution, a temperature gradient, a thermal-dose distribution, or a thermal-dose gradient; and
comparing the thermal-property distribution in an MRI thermal-metric map at each time in the time sequence of the multiple MRI thermal-metric maps with the thermal-property distributions in one or more of the multiple MRI thermal-metric maps earlier in the time sequence, and determining spatial evolution of HIFU-histotripsy-induced liquefaction of the biological material within the target volume over the time interval.

16. A method comprising:
applying high-intensity focused ultrasound (HIFU) histotripsy to a mass of biological material in order to mechanically fractionate a target volume of the biological material within the mass;
concurrently with applying the HIFU histotripsy to the mass of biological material, acquiring magnetic resonance imaging (MRI) data of the mass of biological material in a region including the target volume;
identifying in the acquired MRI data features corresponding to HIFU-histotripsy-induced mechanical fractionation of the biological material within the mass;
based on the identified features in the acquired MRI data, monitoring spatial and temporal progress of HIFU-histotripsy-induced mechanical fractionation of the biological material within the target volume; and
based on the identified features in the acquired MRI data, controlling subsequent application of the HIFU histotripsy to the mass of biological material,
wherein controlling subsequent application of the HIFU histotripsy to the mass of biological material comprises: providing feedback control to application of the HIFU histotripsy to the mass of biological material, wherein the feedback control is applied to the HIFU histotripsy according to at least one of an automatic control process or a manual control process, and wherein the acquired MRI data are one or more MRI renderings of the mass of biological material in a region including the target volume, wherein the identified features in the acquired MRI data are contrasting features in at least one of the one or more MRI renderings, the contrasting features corresponding to a portion of mechanically fractionated biological material within the mass, and wherein, based on the identified features in the acquired MRI data, controlling subsequent application of the HIFU histotripsy to the mass of biological material further comprises:

identifying at least a first feature of the contrasting features as mechanically fractionated biological material within the target volume;

identifying at least a second feature of the contrasting features as intact biological material within the target volume; and adjusting application of the HIFU histotripsy to cause mechanical fractionation of the intact biological material within the target volume, wherein adjusting application of the HIFU histotripsy is at least one of: (i) adjusting a spatial location of a focal point of the HIFU histotripsy, (ii) adjusting a duration of the HIFU histotripsy, (iii) adjusting HIFU pulse parameters, (iv) adjusting HIFU pulse power, or (v) adjusting HIFU pulse duty cycle.

17. The method of claim 16, wherein applying the HIFU histotripsy to the target volume comprises applying boiling histotripsy (BH) to the target volume.

18. The method of claim 16, wherein acquiring the MRI data comprises:
acquiring one or more MRI renderings of the target volume.

19. The method of claim 18, wherein each of the one or more MRI renderings is one of: (i) a diffusion-weighted image, (ii) a T1-weighted image, (iii) a T2-weighted image, (iv) a proton density-weighted image, (v) a T1 map, (vi) a T2 map, (vii) a T1*-weighted image, (viii) a T2*-weighted image, (ix) a T2* map, (x) a T1-p-weighted image, (xi) a fluid attenuated inversion recovery (FLAIR) image, (xii) a susceptibility-weighted image (SWI), (xiii) a diffusion map, or (xiv) a combined MRI rendering of at least two of (i)-(xiii).

20. The method of claim 18, wherein acquiring the one or more MRI renderings comprises:
acquiring a time sequence of multiple MRI renderings during a time interval that is concurrent with applying the HIFU histotripsy to the target volume, the method further comprising:
based on features in the acquired MRI data, monitoring spatial and temporal progress of HIFU-histotripsy-induced mechanical fractionation of the target volume by:
comparing contrasting features in an MRI rendering at each time in the time sequence of the multiple MRI renderings with contrasting features in one or more of the multiple MRI renderings earlier in the time sequence, and determining spatial evolution of HIFU-histotripsy-induced mechanical fractionation of the target volume over the time interval.

21. The method of claim 18, further comprising:
identifying a boundary between the first feature and the second feature as a physical boundary between the mechanically fractionated biological material and the intact biological material.

22. The method of claim 16, further comprising infusing the target volume with a contrast agent prior to or while acquiring the MRI data.

23. The method of claim 17, wherein acquiring the MRI data comprises:
acquiring one or more MRI thermal-metric maps of the target volume, wherein each of the one or more MRI thermal-metric maps is one of an MRI temperature map or an MRI thermal dose map.

* * * * *